(12) United States Patent
Stromberg et al.

(10) Patent No.: US 10,161,003 B2
(45) Date of Patent: Dec. 25, 2018

(54) METHODS AND APPARATUS THAT INCREASE SEQUENCING-BY-BINDING EFFICIENCY

(71) Applicant: OMNIOME, INC., San Diego, CA (US)

(72) Inventors: Sean Stromberg, San Diego, CA (US); John Vieceli, San Diego, CA (US); Kandaswamy Vijayan, San Diego, CA (US); Arnold Oliphant, Morgan Hill, CA (US)

(73) Assignee: Omniome, Inc., San Diego, CA (US)

( * ) Notice: Subject to any disclaimer, the term of this patent is extended or adjusted under 35 U.S.C. 154(b) by 0 days.

(21) Appl. No.: 15/922,787

(22) Filed: Mar. 15, 2018

(65) Prior Publication Data

US 2018/0305749 A1 Oct. 25, 2018

Related U.S. Application Data

(63) Continuation-in-part of application No. 15/712,632, filed on Sep. 22, 2017, now Pat. No. 9,951,385.

(60) Provisional application No. 62/489,610, filed on Apr. 25, 2017, provisional application No. 62/526,514, filed on Jun. 29, 2017.

(51) Int. Cl.
| | | |
|---|---|---|
| *C12Q 1/68* | (2018.01) | |
| *C12Q 1/6874* | (2018.01) | |
| *C12Q 1/6853* | (2018.01) | |

(52) U.S. Cl.
CPC ......... *C12Q 1/6874* (2013.01); *C12Q 1/6853* (2013.01)

(58) Field of Classification Search
CPC ...................................................... C12Q 1/68
See application file for complete search history.

(56) References Cited

U.S. PATENT DOCUMENTS

| | | |
|---|---|---|
| 5,302,509 A | 4/1994 | Cheeseman |
| 5,614,365 A | 3/1997 | Tabor et al. |
| 6,485,909 B1 | 11/2002 | Hong et al. |
| 6,720,177 B2 | 4/2004 | Ghadiri et al. |
| 6,828,094 B2 | 12/2004 | Kilger et al. |
| 6,908,736 B1 | 6/2005 | Densham |
| 7,008,766 B1 | 3/2006 | Densham |
| 7,057,026 B2 | 6/2006 | Barnes et al. |
| 7,223,540 B2 | 5/2007 | Pourmand et al. |
| 7,264,934 B2 | 9/2007 | Fuller |
| 7,329,492 B2 | 2/2008 | Hardin et al. |
| 7,414,116 B2 | 8/2008 | Milton et al. |
| 7,427,673 B2 | 9/2008 | Balasubramanian et al. |
| 7,449,297 B2 | 11/2008 | Freije et al. |
| 7,455,971 B2 | 11/2008 | Chee et al. |
| 7,476,503 B2 | 1/2009 | Turner et al. |
| 7,482,120 B2 | 1/2009 | Buzby |
| 7,544,794 B1 | 6/2009 | Benner |
| 7,604,963 B2 | 10/2009 | Densham |
| 7,635,578 B2 | 12/2009 | Ju et al. |
| 7,713,698 B2 | 5/2010 | Li et al. |
| 7,790,869 B2 | 9/2010 | Li et al. |
| 7,871,771 B2 | 1/2011 | Fuller et al. |
| 7,888,073 B2 | 2/2011 | Densham |
| 7,939,264 B1 | 5/2011 | Densham et al. |
| 7,956,171 B2 | 6/2011 | Siddiqi |
| 8,034,923 B1 | 10/2011 | Benner et al. |
| 8,071,755 B2 | 12/2011 | Efcavitch et al. |
| 8,088,575 B2 | 1/2012 | Li et al. |
| 8,133,672 B2 | 3/2012 | Bjornson et al. |
| 8,236,532 B2 | 8/2012 | Ronaghi et al. |
| 8,298,792 B2 | 10/2012 | Meng et al. |
| 8,535,881 B2 | 2/2013 | Bjornson et al. |
| 8,399,196 B2 | 3/2013 | Hoser |
| 8,481,266 B2 | 7/2013 | Shao et al. |
| 8,603,741 B2 | 12/2013 | Emig et al. |
| 8,632,975 B2 | 1/2014 | Vander Horn et al. |
| 8,652,781 B2 | 2/2014 | Korlach et al. |

(Continued)

FOREIGN PATENT DOCUMENTS

| | | |
|---|---|---|
| EP | 1115848 A1 | 7/2001 |
| WO | WO-90/013666 A1 | 11/1990 |

(Continued)

OTHER PUBLICATIONS

Agnarsson, et al., "On-chip modulation of evanescent illumination and live-cell imaging with polymer waveguides." Optics Express, Nov. 7, 2011, vol. 19, No. 23: 22929-22935.

Anker, et al., "Biosensing with Plasmonic Nanosensors," Nature Materials 7, No. 6 (Jun. 2008): 442-453.

APCH231: Chemical Analysis Complexometric Titrations EDTA, notes compiled by Dr. C. Southway, p. 30-42 (http://cheminnerweb.ukzn.ac.za/libraries/apch231_h_govenders_notes/apch231_edta.sfib.ashx).

Bandwar et al., "Peculiar 2-Aminopurine Fluorescence Monitors the Dynamics of Open Complex Formation by Bacteriophage T7 RNA Polymerase." The Journal of Biological Chemistry, vol. 275, No. 17, Issue of 27: 14075-14082, 2001.

Brockman, et al. "A Multistep Chemical Modification Procedure to Create DNA Arrays on Gold Surfaces for the Study of Protein—DNA Interactions with Surface Plasmon Resonance Imaging." Journal of the American Chemical Society. Sep. 1999, 121: 8044-8051.

(Continued)

*Primary Examiner* — Aaron A Priest
(74) *Attorney, Agent, or Firm* — Zachary L. Terranova; Mintz Levin Cohn Ferris Glovsky and Popeo, P.C.

(57) ABSTRACT

A method of determining a nucleic acid sequence that includes steps of: (a) contacting a primed template nucleic acid with a series of mixtures for forming ternary complexes, wherein each of the mixtures includes a polymerase and nucleotide cognates for at least two different base types suspected of being present at the next template position of the template nucleic acid; (b) monitoring the next template position for ternary complexes formed by the series of mixtures, wherein a signal state indicates presence or absence of ternary complex formed at the next template position by each individual mixture, thereby determining a series of signal states that encodes a base call for the next template position; and (c) decoding the series of signal states to distinguish a correct base call for the next template position from an error in the base call.

29 Claims, No Drawings

(56) References Cited

U.S. PATENT DOCUMENTS

| | | |
|---|---|---|
| 8,658,365 B2 | 2/2014 | Bjornson et al. |
| 8,703,461 B2 | 4/2014 | Peris et al. |
| 8,808,989 B1 | 8/2014 | Efcavitch et al. |
| 8,911,972 B2 | 12/2014 | Chaisson et al. |
| 8,986,930 B2 | 3/2015 | Fedorov et al. |
| 9,222,132 B2 | 12/2015 | Drmanac |
| 9,255,258 B2 | 2/2016 | Vander Horn et al. |
| 9,279,154 B2 | 3/2016 | Previte et al. |
| 9,279,155 B2 | 3/2016 | Bjornson et al. |
| 9,353,412 B2 | 5/2016 | He et al. |
| 9,382,584 B2 | 7/2016 | Huang |
| 9,399,798 B2 | 7/2016 | Stupi et al. |
| 9,453,258 B2 | 9/2016 | Kain et al. |
| 9,523,125 B2 | 12/2016 | Drmanac |
| 9,556,480 B2 | 1/2017 | Turner et al. |
| 9,695,471 B2 | 7/2017 | Beechem et al. |
| 9,719,073 B2 | 8/2017 | Emig et al. |
| 9,951,385 B1 | 4/2018 | Vijayan et al. |
| 2006/0051807 A1 | 3/2006 | Fuller |
| 2006/0292583 A1 | 12/2006 | Schneider et al. |
| 2007/0009925 A1 | 1/2007 | Fang et al. |
| 2009/0061447 A1 | 3/2009 | Schneider et al. |
| 2009/0286245 A1* | 11/2009 | Bjornson ............. C12Q 1/6869 435/6.18 |
| 2010/0092960 A1* | 4/2010 | Fehr ................... C12Q 1/6869 435/6.11 |
| 2010/0111768 A1 | 5/2010 | Banerjee et al. |
| 2010/0173303 A1 | 7/2010 | Ronaghi |
| 2010/0316999 A1 | 12/2010 | Densham et al. |
| 2010/0317012 A1 | 12/2010 | Ju et al. |
| 2010/0330570 A1 | 12/2010 | Vander Horn et al. |
| 2011/0008794 A1 | 1/2011 | Schneider et al. |
| 2011/0237464 A1 | 9/2011 | Cunningham et al. |
| 2012/0270305 A1 | 10/2012 | Reed et al. |
| 2013/0053252 A1 | 2/2013 | Xie et al. |
| 2013/0079232 A1 | 3/2013 | Kain et al. |
| 2013/0165328 A1* | 6/2013 | Previte ................. C12Q 1/6874 506/2 |
| 2014/0127680 A1 | 5/2014 | Emig et al. |
| 2014/0234940 A1 | 8/2014 | Peris et al. |
| 2015/0031560 A1 | 1/2015 | Fabani et al. |
| 2015/0087537 A1* | 3/2015 | Hubbell .............. C12Q 1/6869 506/4 |
| 2015/0169824 A1 | 6/2015 | Kermani et al. |
| 2015/0184238 A1 | 7/2015 | Eshoo |
| 2016/0010150 A1 | 1/2016 | Emig |
| 2016/0032379 A1 | 2/2016 | Gloeckner |
| 2016/0168633 A1 | 6/2016 | Previte et al. |
| 2016/0177384 A1 | 6/2016 | Bjornson et al. |
| 2016/0208318 A1 | 7/2016 | Vander Horn et al. |
| 2017/0022553 A1* | 1/2017 | Vijayan ............... C12Q 1/6869 |
| 2017/0114403 A1 | 4/2017 | Ju et al. |
| 2017/0292157 A1 | 10/2017 | Drmanac |
| 2017/0314064 A1 | 11/2017 | Iyidogan et al. |
| 2018/0044727 A1 | 2/2018 | Vijayan et al. |
| 2018/0080073 A1 | 3/2018 | Vijayan et al. |

FOREIGN PATENT DOCUMENTS

| | | |
|---|---|---|
| WO | WO-91/06678 A1 | 5/1991 |
| WO | WO-01/016375 A2 | 3/2001 |
| WO | WO-01/016375 A3 | 3/2001 |
| WO | WO-02/04680 A2 | 1/2002 |
| WO | WO-02/04680 A3 | 1/2002 |
| WO | WO-2005/019476 A1 | 3/2005 |
| WO | WO-2005/065814 A1 | 7/2005 |
| WO | WO-2005/121363 A2 | 12/2005 |
| WO | WO-2005/121363 A3 | 12/2005 |
| WO | WO-2007/091077 A1 | 8/2007 |
| WO | WO-2007/123744 A2 | 11/2007 |
| WO | WO-2007/123744 A3 | 11/2007 |
| WO | WO-2009/145820 A2 | 12/2009 |
| WO | WO-2009/145820 A3 | 12/2009 |
| WO | WO-2009/145828 A2 | 12/2009 |
| WO | WO-2009/145828 A3 | 12/2009 |
| WO | WO-2010/068884 A2 | 6/2010 |
| WO | WO-2010/068884 A3 | 6/2010 |
| WO | WO-2010/111690 A2 | 9/2010 |
| WO | WO-2010/111690 A3 | 9/2010 |
| WO | WO-2010/141390 A2 | 12/2010 |
| WO | WO-2010/141390 A3 | 12/2010 |
| WO | WO-2010141390 A3 * | 8/2011 ........... C12Q 1/6827 |
| WO | WO-2011/159942 A1 | 12/2011 |
| WO | WO-2012/166742 A2 | 12/2012 |
| WO | WO-2012/166742 A3 | 12/2012 |
| WO | WO-2013/096692 A1 | 6/2013 |
| WO | WO-2014/114665 A1 | 7/2014 |
| WO | WO-2017/014762 A1 | 1/2017 |
| WO | WO-2017/190018 A1 | 11/2017 |
| WO | WO-2018/035134 A1 | 2/2018 |

OTHER PUBLICATIONS

Brown, et al., "Pre-Steady-State Kinetic Analysis of Truncated and Full-Length *Saccharomyces cerevisiae* DNA Polymerase Eta." Journal of Nucleic Acids, 2010, Article ID 871939, 11 pages.

Campagnola, et al., "High-throughput Screening Identification of Poliovirus RNA-dependent RNA Polymerase Inhibitors." Antiviral Res. Sep. 2011; 91(3):241-251.

Chan, et al., "A general method for discovering inhibitors of protein-DNA interactions using photonic crystal biosensors." ACS Chem Biol. Jul. 18, 2008; 3(7): 437-448.

Chen, et al., "The History and Advances of Reversible Terminators Used in New Generations of Sequencing Technology." Genomics Proteomics Bioinformatics, 2013, 11(1): 34-40.

Chin, Y. E. et al., "The Effect of Divalent Nickel (Ni2+) on in Vivo DNA Replication by DNA Polymerase a1," Cancer Research, May 1, 1994, vol. 54, pp. 2337-2341.

Choi, et al., "EML4-ALK Mutations in Lung Cancer that Confer Resistance to ALK Inhibitors." N. Engl. J. Med. (2010)18:1734-1739.

Concepcion, "Label-Free Detection of Biomolecular Interactions Using BioLayer Interferometry for Kinetic Characterization." Combinatorial Chemistry and High Throughput Screening. 2009, 12(8):791-800; abstract only.

Crumpacker, "Mechanism of action of foscarnet against viral polymerases." American Journal of Medicine, Feb. 14, 1992, vol. 92, Issue 2, Supplement 1, pp. S3-S7, abstract only.

Datta, K. et al. (Feb. 21, 2003). "Salt dependence of DNA binding by Thermus aquaticus and *Escherichia coli* DNA polymerases," J Biol Chem 278(8):5694-5701.

Deredge, D.J. et al. (Aug. 13, 2010, e-published Jun. 15, 2010). "The glutamate effect on DNA binding by pol I DNA polymerases: osmotic stress and the effective reversal of salt linkage," J Mol Biol 401(2):223-238.

Doublie, S. et al., "An open and closed case for all polymerases", Structure, Feb. 1999, 7:R31-R35.

Dunlap, C.A. et al. "Use of 2-Aminopurine and Tryptophan Fluorescence as Probes in Kinetic Analyses of DNA Polymerase Beta." Biochemistry, 2002, 41: 11226-11235.

Dzantiev, L. et al. "A conformational change in *E. coli* DNA polymerase I (Klenow fragment) is induced in the presence of a dNTP complementary to the template base in the active site", Biochemistry, 2000, 39(2):356-361.

Engstrom, et al. (Oct. 15, 2006). "A label-free continuous total-internal-reflection-fluorescence-based immunosensor." Analytical Biochemistry 357(2):159-166.

Eriksson, Oberg, Wahren, "Pyrophosphate analogues as inhibitors of DNA polymerases of cytomegalovirus, herpes simplex virus and cellular origin." Biochimica et Biophysica Acta (1982), 696(2): 115-123.

Escobedo, et al., "Integrated nanohole array surface plasmon resonance sensing device using a dual-wavelength source." Journal of Micromechanics and Microengineering, vol. 21, No. 11, Oct. 3, 2011.

(56) References Cited

OTHER PUBLICATIONS

Espinoza-Herrera, et al., "Following DNA Chain Extension and Protein Conformational Changes in Crystals of a Y-Family DNA Polymerase via Raman Crystallography." Biochemistry, Jul. 23, 2013, 52(29), abstract only.
Fang, et al., "Genome-wide mapping of methylated adenine residues in pathogenic Escherichia coli using single-molecule real-time sequencing." Dec. 2012, vol. 30, No. 12, 1232-1243.
Favicchio et al., "Fluorescence Spectroscopy and Anisotrophy in the analysis of DNA-Protein Interactions." Methods in Molecular Biology, DNA-Protein Interactions, vol. 543, 2009, 589-611.
Federley, Richard George, "New insights into the mechanism of dna replication on unmodified and benzo[a]pyrene modified templates using surface plasmon resonance," Wayne State University Dissertations, 2011, Paper 235, 208 pages.
Fuller, et al., "The challenges of Sequencing by synthesis." Nature Biotechnology, vol. 27, No. 11, Nov. 2009, pp. 1013-1023.
Horn, et al., "EML4-ALK: Honing in on a New Target in Non-Small-Cell Lung Cancer." Journal of Clinical Oncology. Sep. 10, 2009. vol. 27, No. 26, p. 4232-4235.
Hoshino, et al., "Effect of Ultrasound on DNA Polymerase Reactions: Monitoring on a 27-MHz Quartz Crystal Microbalance." Biomacromolecules, 2006, 7(3), pp. 682-685, abstract only.
Hutter, et al., "Labeled Nucleoside Triphosphates with Reversibly Terminating Aminoalkoxyl Groups." vol. 29, Issue 11-12, 2010, abstract only.
International Search Report and Written Opinion dated Feb. 9, 2016, issued in International Application No. PCT/ US2015/041415, 11 pages.
Ion Torrent: "Ion Torrent Amplicon Sequencing", Internet Citation [Online] Apr. 4, 2011 (Apr. 4, 2011), pp. 1-5, Retrieved from the Internet: URL: http://www.iontorrent.com/lib/images/PDFs/amplicon_application_note_040411.pdf>.
Jindal, et al., "Suramin affects DNA Synthesis in HeLa Cells by Inhibition of DNA Polymerases." Cancer Research, Dec. 15, 1990, 50:7754-7757.
Jochmans, et al., "Indolopyridones Inhibit Human Immunodeficiency Virus Reverse Transcriptase with a Novel Mechanism of Action." Journal of Virology, Dec. 2006, vol. 80, No. 24: 12283-12292.
Kaplan, "Photolabile chelators for the rapid photorelease of divalent cations." Proc. Natl. Acad. Sci. USA, Sep. 1988, vol. 85: 6571-6575.
Kaushik, et al., "Biochemical Analysis of Catalytically Crucial Aspartate Mutants of Human Immunodeficiency Virus Type 1 Reverse Transcriptase." Biochemistry, 1996, 35:11536-11546.
Kim, Dong-Sun, "An FET-type charge sensor for highly sensitive detection of DNA sequence." Biosensors and Bioelectronics, Microsensors and Microsystems 2003, 20, No. 1 (Jul. 30, 2004): 69¬74, abstract only.
Klenow, H. et al. (May 1, 1969). "Effect of monovalent cations on the activity of the DNA polymerase of Escherichia coli B," Eur J Biochem 9(1):133-141.
Kumar, et al., "Altered Order of Substrate Binding by DNA Polymerase X from African Swine Fever Virus." Biochemistry 2008: 7875-7887.
Leinbach, et al., "Mechanism of phosphonoacetate inhibition of herpesvirus-induced DNA polymerase." Biochemistry, 1976, 15(2), pp. 426-430, abstract only.
Lutz, et al. "An in vitro screening technique for DNA polymerases that can incorporate modified nucleotides. Pseudothymidine as a substrate for thermostable polymerases." Nucleic Acids Research, 1999, vol. 27, No. 13: 2792-2798.
Maga, et al., "HIV-1 RT Inhibitors with a Novel Mechanism of Action: NNRTIs that Compete with the Nucleotide Substrate." Viruses 2010, 2(4): 880-899.
Maga, et al., "Selective Interaction of the Human Immunodeficiency Virus Type 1 Reverse Transcriptase Nonnucleoside Inhibitor Efavirenz and Its Thio-Substituted Analog with Different Enzyme-Substrate Complexes." Antimicrobial Agents and Chemotherapy, May 2000, vol. 44, No. 5: 1186-1194.
Mano, H. "Non-solid oncogenes in solid tumors: EML4-ALK fusion genes in lung cancer." (2008), Cancer Sci., 99:2349-2355.
Markiewicz, et al. "Single-Molecule Microscopy Reveals New Insights into Nucleotide Selection by DNA Polymerase I." Nucleic Acids Research, 2012, vol. 40, No. 16: 7975-7984.
Masheyekhi, et al., "Analysis of Read-Length Limiting Factors in Pyrosequencing Chemistry." Anal Biochem. Apr. 15, 2007; 363(3): 275-287.
Namasivayam, "Light-Induced Molecular Cutting: Localized Reaction on a Single DNA Molecule." Anal. Chem. 2003, 75: 4118-4194.
Nath, N. et al. "Label free colorimetric biosensing using nanoparticles." Jul. 2004; 14(4):377-89, abstract only.
Nazirizadeh, et al., "Low-cost label-free biosensors using photonic crystals embedded between crossed polarizers." Optics Express, Aug. 30, 2010, vol. 18, No. 18, 19120-19128.
Nikiforov, "Oligonucleotides labeled with single flurophores as sensors for deoxynucleotide triphosphate binding by DNA polymerases." Analytical Biochemistry 444 (2014): 60-66.
Patel, P.H. et al. "Insights into DNA Polymerization Mechanisms from Structure and Function Analysis of HIV-1 Reverse Transcriptase." 1995 Biochemistry 34:5351-5363, abstract only.
Peletskaya, et al. "Cross-Linking of the Fingers Subdomain of Human Immunodeficiency Virus Type 1 Reverse Transcriptase to Template-Primer." Journal of Virology, Oct. 2001, vol. 75, No. 19: 9435-9445.
Pitta, et al., "Synthesis and HIV-1 RT inhibitory action of novel (4/6-substituted benzo[d]thiazol-2-yl) thiazolidin-4-ones. Divergence from the non-competitive inhibition mechanism." J. Enzyme Inhib. Med. Chem. 28(10):113-122(2013), abstract only.
Potapova, I.A et al. (Dec. 1990). "NaF and mononucleotides as inhibitors of 3'-5'-exonuclease activity and stimulators of polymerase activity of E. coli DNA polymerase I Klenow fragment," FEBS Lett 277(1-2):109-111.
Potapova, et al., "Interaction of dNTP, pyrophosphate and their analogs with the dNTP-binding sites of E. coli DNA polymerase I Klenow fragment and human DNA polymerase." Dec. 17, 1990, vol. 277, Issues 1-2, pp. 194-196.
Puttaswamy, "Optical Method for Measuring Spatial pH Change on Conductive Microelectrodes." KTH, Royal Institute of Technology, Stockholm, Sweden, 66 pages.
Ren, et al., "Inhibition of Klenow DNA polymerase and poly(A)-specific ribonuclease by aminoglycosides." RNA (2002), 8:1393-1400.
Richard, A.J. et al. (Oct. 2006, e-published Aug. 30, 2006). "Thermal stability landscape for Klenow DNA polymerase as a function of pH and salt concentration," Biochim Biophys Acta 1764(10):1546-1552.
Roettger, et al., Mismatched and Matched dNTP Incorporation by DNA Polymerase p Proceed via Analogues Kinetic Pathways, Biochemistry, 2008, 47: 9718-9727.
Santoso, Y. et al. (Jan. 12, 2010). "Conformational transitions in DNA polymerase I revealed by single-molecule FRET," Proceedings of the National Academy of Sciences, 107(2):715-720.
Schadt, et al., "Modeling Kinetic rate variation in third generation DNA sequencing data to detect putative modifications to DNA bases." Genome Research, 2013:129-141.
Schultz, et al., "Single-target molecule detection with nonbleaching multicolor optical immunolabels." PNAS, Feb. 1, 2000, vol. 96, No. 3:996-1001.
Sen, R. et al. "Intrinsic fluorescence of E. coli RNA polymerase as a probe for its conformational changes during transcription initiation." Biochem Biophys Res Commun. Jun. 15, 1994; 201(2):820-8.
Soda, et al., "Identification of the transforming EML4-ALK fusion gene in non-small-cell lung cancer." Aug. 2, 2007. vol. 448:561-566.
Star, et al., "Electronic Detection of Specific Protein Binding Using Nanotube FET Devices." Nano Letters 3, No. 4 (Apr. 1, 2003):459-463.
Su, "Surface Plasmon Resonance Spectroscopy and Quartz Crystal Microbalance Study of Streptavidin Film Structure effects on

(56) References Cited

OTHER PUBLICATIONS

Biotinylated DNA Assembly and Target DNA Hybridization." Langmuir, 2005, 21(1), pp. 348-353, abstract only.

Tsai, Y. C. et al. (Jan. 1, 2009). "Site-specific labeling of T7 DNA polymerase with a conformationally sensitive fluorophore and its use in detecting single-nucleotide polymorphisms", Analytical Biochemistry, 384(1):136-144.

Vaidyanathan, et al., "Binding kinetics of DNA-protein interaction using surface plasmon resonance." Protocol Exchange, May 22, 2013, 11 pages.

Vaidyanathan et al. "Binary and ternary binding affinities between exonuclease-deficient Klenow fragment (Kf-exo(-)) and various arylamine DNA lesions characterized by surface plasmon resonance." Chem Res Toxicol. Aug. 20, 2012; 25(8): 1568-1570.

Vollmer, F. et al. "Whispering-gallery-mode biosensing: label-free detection down to single molecules." Nature Methods, vol. 5, No. 7, Jul. 2008:591-596.

Walsh, et al., "Synthetic Nucleotides as Probes of DNA Polymerase Specificity." Journal of Nucleic Acids, vol. 2012, Article ID 530963, 17 pages.

Washington, et al., "Human DNA Polymerase Utilizes Different Nucleotide Incorporation Mechanisms Dependent upon the Template Base." Molecular and Cellular Biology, Jan. 2004, vol. 24, No. 2: 936-943.

Xia, S. et al., "DNA Mismatch Synthesis Complexes Provide Insights into Base Selectivity of a B family DNA Polymerase." J Am Chem Soc. Jan. 9, 2013; 135(1): 193-202.

Yuzenkova, et al., "Tagetitoxin inhibits transcription by stabilizing pre-translocated state of the elongation complex." Nucleic Acids Research, 2013:1-9.

International Search Report dated Nov. 7, 2017, for PCT Application No. PCT/US2017/046976, filed Aug. 15, 2017, 6 pages.

Written Opinion dated Nov. 7, 2017, for PCT Application No. PCT/US2017/046976, filed Aug. 15, 2017, 8 pages.

International Search Report dated Jul. 28, 2017, for PCT Application No. PCT/US2017/030143, filed Apr. 28, 2017, 3 pages.

Written Opinion dated Jul. 28, 2017, for PCT Application No. PCT/US2017/030143, filed Apr. 28, 2017, 5 pages.

Previte M.J. et al. (Jan. 23, 2015). "DNA sequencing using polymerase substrate-binding kinetics," Nat Commun 6:5936.

Jalali-Yazdi, F. et al. (Mar. 14, 2016, e-published Feb. 23, 2016). "High-Throughput Measurement of Binding Kinetics by mRNA Display and Next-Generation Sequencing," *Angew Chem Int Ed Engl* 55(12):4007-4010.

International Search Report dated Jun. 19, 2018, for PCT Application No. PCT/US2018/029420, filed Apr. 25, 2018, 6 pages.

Written Opinion dated Jun. 19, 2018, for PCT Application No. PCT/US2018/029420, filed Apr. 25, 2018, 9 pages.

\* cited by examiner

METHODS AND APPARATUS THAT INCREASE SEQUENCING-BY-BINDING EFFICIENCY

This application is a continuation-in-part of U.S. patent application Ser. No. 15/712,632, filed Sep. 22, 2017 and claims the benefit of U.S. Provisional Application No. 62/489,610, filed Apr. 25, 2017 and U.S. Provisional Application No. 62/526,514, filed Jun. 29, 2017, each of which is hereby incorporated by reference in its entirety.

BACKGROUND

The present disclosure relates generally to molecular analysis and diagnostics, and has specific applicability to nucleic acid sequencing.

The time required to sequence a human genome has dropped precipitously in the last decade. The procedure, which used to take several years and millions of dollars to perform, can now be completed in a few days, for a few thousand dollars. Although the rate of improvement has been impressive, and has indeed outpaced the previous bellwether of rapid innovation, semiconductor fabrication, the currently available commercial methods are still unsatisfactory for many clinical applications.

A key clinical hope for sequencing has been to provide important information to develop a reliable diagnosis as to whether a patient has a deadly disease and, moreover, to provide guidance when choosing between expensive or life altering treatment options. For example, sequencing can play a key role in confirming a preliminary cancer diagnosis and helping the patient decide on treatment options such as surgery, chemotherapy or radiation treatment. Although a few days of delay for such confirmation is not likely to adversely impact clinical outcome, there is a significant adverse toll on the emotional and psychological state of the patient who endures the delay.

In other situations, clinical outcome is strongly dependent on a rapid diagnosis. In a handful of cases, sequencing has been used in neonatal intensive care units to identify mystery diseases in newborn infants and lead doctors to otherwise unrecognized treatment options that saved lives. Nevertheless, too many newborns die every year for lack of a timely diagnosis.

Thus, there exist needs for improvements to the accuracy, speed and cost of nucleic acid sequencing. The present invention satisfies these needs and provides related advantages as well.

BRIEF SUMMARY

The present disclosure provides a method of nucleic acid detection, that includes the steps of (a) forming a mixture under ternary complex stabilizing conditions, wherein the mixture includes a primed template nucleic acid, a polymerase and nucleotide cognates of first, second and third base types in the template; (b) examining the mixture to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

Also provided is a method of nucleic acid detection that includes the steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base type base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

The present disclosure further provides a method of nucleic acid detection that includes the steps of (a) contacting a primed template nucleic acid with a polymerase and a first mixture of nucleotides under ternary complex stabilizing conditions, wherein the first mixture includes a nucleotide cognate of a first base type and a nucleotide cognate of a second base type; (b) contacting the primed template nucleic acid with a polymerase and a second mixture of nucleotides under ternary complex stabilizing conditions, wherein the second mixture includes a nucleotide cognate of the first base type and a nucleotide cognate of a third base type; (c) examining products of steps (a) and (b) for signals produced by a ternary complex that includes the primed template nucleic acid, a polymerase and a next correct nucleotide, wherein signals acquired for the product of step (a) are ambiguous for the first and second base type, and wherein signals acquired for the product of step (b) are ambiguous for the first and third base type; (d) disambiguating signals acquired in step (c) to identify a base type that binds the next correct nucleotide. Optionally, to achieve disambiguation (i) the first base type is correlated with presence of signals for the product of step (a) and presence of signals for the product of step (b), (ii) the second base type is correlated with presence of signals for the product of step (a) and absence of signals for the product of step (b), and (iii) the third base type is correlated with absence of signals for the product of step (a) and presence of signals for the product of step (b).

Also provided is a method of nucleic acid detection that includes the steps of (a) contacting a primed template nucleic acid with a first mixture including a polymerase, a nucleotide cognate of a first base type in the template and a nucleotide cognate a second base type in the template, wherein the contact occurs in a binding reaction that (i) stabilizes ternary complexes including the primed template nucleic acid, the polymerase and a next correct nucleotide, and (ii) prevents incorporation of the next correct nucleotide into the primer; (b) examining the binding reaction to determine whether a ternary complex formed; (c) subjecting the primed template nucleic acid to a repetition of steps (a) and (b), wherein the first mixture is replaced with a second mixture, the second mixture including a polymerase, a nucleotide cognate of the first base type in the template and a nucleotide cognate of a third base type in the template; and (d) identifying the next correct nucleotide for the primed template nucleic acid using the examination of the binding reaction, or the product thereof, wherein (i) the next correct nucleotide is identified as a cognate of the first base type if ternary complex is detected in step (b) and detected in the repetition of step (b), (ii) the next correct nucleotide is identified as a cognate of the second base type if ternary complex is detected in step (b) and undetected in the repetition of step (b), and (iii) the next correct nucleotide is identified as a cognate of the third base type if ternary complex is undetected in step (b) and detected in the repetition of step (b).

In particular embodiments, the steps of a nucleic acid detection method set forth herein can be repeated to interrogate several different positions in a template nucleic acid. Accordingly, this disclosure provides a method for sequencing a nucleic acid that includes the steps of (a) forming a mixture under ternary complex stabilizing conditions, wherein the mixture includes a primed template nucleic acid, a polymerase and nucleotide cognates of first, second and third base types in the template; (b) examining the mixture to determine whether a ternary complex formed; (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) for the primed template nucleic acid that comprises the extended primer.

The present disclosure also provides a method of determining a nucleic acid sequence that includes steps of: (a) contacting a primed template nucleic acid with a series of mixtures for forming ternary complexes, wherein each of the mixtures includes a polymerase and nucleotide cognates for at least two different base types suspected of being present at the next template position of the template nucleic acid; (b) monitoring the next template position for ternary complexes formed by the series of mixtures, wherein a signal state indicates presence or absence of ternary complex formed at the next template position by each individual mixture, thereby determining a series of signal states that encodes a base call for the next template position; and (c) decoding the series of signal states to distinguish a correct base call for the next template position from an error in the base call.

In particular embodiments, the steps of a nucleic acid detection method set forth herein can be repeated to interrogate several different positions in a template nucleic acid. Accordingly, this disclosure provides a method for sequencing a nucleic acid that includes the steps of (a) forming a mixture under ternary complex stabilizing conditions, wherein the mixture includes a primed template nucleic acid, a polymerase and nucleotide cognates of first, second and third base types in the template, wherein each nucleotide cognate of first, second and third base type in the template is capable of forming a ternary complex that is differentially detectable (i.e., a ternary complex formed with a nucleotide cognate of the first, second or third base type, respectively may be identified as such and may be identified as different from a ternary complex formed with a nucleotide cognate of the second or third, first or third, or first or second base types, respectively); (b) examining the mixture to determine whether a ternary complex formed; (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) for the primed template nucleic acid that comprises the extended primer.

Also provided by this disclosure is a method for sequencing a nucleic acid that includes the steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base type base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) for the primed template nucleic acid that comprises the extended primer.

In further embodiments a method of nucleic acid sequencing can include the steps of (a) contacting a primed template nucleic acid with a polymerase and a first mixture of nucleotides under ternary complex stabilizing conditions, wherein the first mixture includes a nucleotide cognate of a first base type and a nucleotide cognate of a second base type; (b) contacting the primed template nucleic acid with a polymerase and a second mixture of nucleotides under ternary complex stabilizing conditions, wherein the second mixture includes a nucleotide cognate of the first base type and a nucleotide cognate of a third base type; (c) examining products of steps (a) and (b) for signals produced by a ternary complex that includes the primed template nucleic acid, a polymerase and a next correct nucleotide, wherein signals acquired for the product of step (a) are ambiguous for the first and second base type, and wherein signals acquired for the product of step (b) are ambiguous for the first and third base type; (d) disambiguating signals acquired in step (c) to identify a base type that binds the next correct nucleotide; (e) adding a next correct nucleotide to the primer of the primed template nucleic acid after step (c), thereby producing an extended primer; and (f) repeating steps (a) through (e) for the primed template nucleic acid that comprises the extended primer.

Further still, a method of nucleic acid sequencing can include the steps of (a) contacting a primed template nucleic acid with a first mixture including a polymerase, a nucleotide cognate of a first base type in the template and a nucleotide cognate a second base type in the template, wherein the contact occurs in a binding reaction that (i) stabilizes ternary complexes including the primed template nucleic acid, the polymerase and a next correct nucleotide, and (ii) prevents incorporation of the next correct nucleotide into the primer; (b) examining the binding reaction to determine whether a ternary complex formed; (c) subjecting the primed template nucleic acid to a repetition of steps (a) and (b), wherein the first mixture is replaced with a second mixture, the second mixture including a polymerase, a nucleotide cognate of the first base type in the template and a nucleotide cognate of a third base type in the template; (d) identifying the next correct nucleotide for the primed template nucleic acid using the examination of the binding reaction, or the product thereof, wherein (i) the next correct nucleotide is identified as a cognate of the first base type if ternary complex is detected in step (b) and detected in the repetition of step (b), (ii) the next correct nucleotide is identified as a cognate of the second base type if ternary complex is detected in step (b) and undetected in the repetition of step (b), and (iii) the next correct nucleotide is identified as a cognate of the third base type if ternary complex is undetected in step (b) and detected in the repetition of step (b); (e) adding a next correct nucleotide to the primer of the primed template nucleic acid after step (c), thereby producing an extended primer; and (f) repeating steps (a) through (e) for the primed template nucleic acid that comprises the extended primer.

In embodiments, when a ternary complex is detected/undetected in step (b) and detected/undetected in the repetition of step (b), the ternary complex is detected/undetected in the first iteration of step (b) and detected/undetected in the repetition (i.e., second iteration) of step (b).

This disclosure further provides a method of nucleic acid detection that includes steps of (a) sequentially contacting a primed template nucleic acid with at least four separate mixtures under ternary complex stabilizing conditions, wherein each of the mixtures includes a polymerase and nucleotide cognates for at least two of four different base types in the primed template nucleic acid; (b) examining the at least four separate mixtures to detect ternary complexes; and (c) identifying the next correct nucleotide for the primed template nucleic acid molecule, wherein the next correct nucleotide is identified as a cognate of one of the four different base types if ternary complex is detected in at least two of the mixtures.

In particular embodiments, a method of nucleic acid detection, can include (a) sequentially contacting a primed template nucleic acid with first and second mixtures under ternary complex stabilizing conditions, wherein each of the mixtures includes a polymerase and nucleotide cognates for at least two of four different base types in the primed template nucleic acid, wherein the mixtures differ by at least one type of nucleotide cognate; (b) examining the first and second mixtures separately to detect ternary complexes; and (c) identifying the next correct nucleotide for the primed template nucleic acid molecule, wherein the next correct nucleotide is identified as a cognate of one of the four different base types if ternary complex is detected in the two mixtures.

In particular embodiments, a method of nucleic acid detection, can include (a) sequentially contacting a primed template nucleic acid with first and second mixtures under ternary complex stabilizing conditions, wherein each of the mixtures includes a polymerase and nucleotide cognates for at least two of four different base types in the primed template nucleic acid, wherein the mixtures differ by at least one type of nucleotide cognate; (b) examining the first and second mixtures separately to detect ternary complexes; and (c) identifying the next correct nucleotide for the primed template nucleic acid molecule, wherein the next correct nucleotide is identified as a cognate of one of the four different base types if ternary complex is detected in first mixture but not the second mixture.

In particular embodiments, a method of nucleic acid detection, can include (a) sequentially contacting a primed template nucleic acid with first and second mixtures under ternary complex stabilizing conditions, wherein each of the mixtures includes a polymerase and nucleotide cognates for at least two of four different base types in the primed template nucleic acid, wherein the mixtures differ by at least one type of nucleotide cognate; (b) examining the first and second mixtures separately to detect ternary complexes; and (c) identifying the next correct nucleotide for the primed template nucleic acid molecule, wherein the next correct nucleotide is identified as a cognate of one of the four different base types if ternary complex is detected in the second mixture but not the first mixture.

In particular embodiments, a method of nucleic acid detection, can include (a) sequentially contacting a primed template nucleic acid with first and second mixtures under ternary complex stabilizing conditions, wherein each of the mixtures includes a polymerase and nucleotide cognates for at least two of four different base types in the primed template nucleic acid, wherein the mixtures differ by at least one type of nucleotide cognate; (b) examining the first and second mixtures separately to detect ternary complexes; and (c) identifying the next correct nucleotide for the primed template nucleic acid molecule, wherein the next correct nucleotide is identified as a cognate of one of the four different base types if ternary complex is not detected in the two mixtures.

Also provided is a method of nucleic acid detection that includes steps of (a) contacting a primed template nucleic acid with a polymerase and a first mixture of nucleotides under conditions for stabilizing a ternary complex at a nucleotide position in the template, wherein the first mixture includes a nucleotide cognate of a first base type and a nucleotide cognate of a second base type; (b) contacting the primed template nucleic acid with a polymerase and a second mixture of nucleotides under conditions for stabilizing a ternary complex at the nucleotide position in the template, wherein the second mixture includes a nucleotide cognate of the first base type and a nucleotide cognate of a third base type; (c) contacting the primed template nucleic acid with a polymerase and a third mixture of nucleotides under conditions for stabilizing a ternary complex at the nucleotide position in the template, wherein the third mixture includes a nucleotide cognate of the second base type and a nucleotide cognate of a fourth base type; (d) contacting the primed template nucleic acid with a polymerase and a fourth mixture of nucleotides under conditions for stabilizing a ternary complex at the nucleotide position in the template, wherein the fourth mixture includes a nucleotide cognate of the third base type and a nucleotide cognate of the fourth base type; (e) examining products of steps (a) through (d) for signals produced by a ternary complex that includes the primed template nucleic acid, a polymerase and a next correct nucleotide, wherein signals acquired for the product of step (a) are ambiguous for the first and second base type, wherein signals acquired for the product of step (b) are ambiguous for the first and third base type, wherein signals acquired for the product of step (c) are ambiguous for the second and fourth base type, and wherein signals acquired for the product of step (d) are ambiguous for the third and fourth base type; (f) disambiguating signals acquired in step (e) to identify a base type that binds the next correct nucleotide.

DETAILED DESCRIPTION

The present disclosure provides improved methods for identifying nucleotides in a nucleic acid. In some embodiments, multiple nucleotides are identified via a repetitive sequencing reaction. Various sequencing techniques can be used to read a template nucleic acid, one position at a time, as a primer is elongated along the template via polymerase based synthesis. One such technique, Sequencing By Binding™ (SBB™) methodology, is generally based on repetitive cycles of detecting a stabilized complex that forms at each position along the template (e.g. a ternary complex that includes the primed template, a polymerase, and a cognate nucleotide for the position), under conditions that prevent covalent incorporation of the cognate nucleotide into the primer, and then extending the primer to allow detection of the next position along the template. In SBB™ methods, detection of the nucleotide at each position of the template occurs prior to extension of the primer to the next position.

Generally, SBB™ methodology is used to distinguish four different nucleotide types that can be present at positions along a nucleic acid template. The type of nucleotide at each position can be distinguished by uniquely labelling each type of ternary complex (i.e. different types of ternary complexes differing in the type of nucleotide it contains) or by separately delivering the reagents needed to form each type of ternary complex. The two configurations provide different advantages when compared to each other. For example, the former configuration has the relative disadvantage of requiring complex detection hardware having four separate detection channels (instead of only one channel which can be used in the latter configuration). The latter configuration has the relative disadvantage of consuming more time and reagent to accommodate four different reagent deliveries (instead of the single reagent delivery possible in the former configuration).

The present disclosure provides alternative reaction configurations and reagent compositions that can minimize or avoid the above disadvantages. In a particular embodiment, an SBB™ reaction cycle is carried out with only a subset of the possible nucleotide types that are capable of serving as cognates for the diversity of base types expected to occur in the template being sequenced. In this embodiment, the identity of an omitted nucleotide can be imputed. For example, a DNA template can be subjected to an SBB™ reaction cycle with only three nucleotide types. The presence of cognates for the three types of nucleotides can be distinguished at individual positions of the template according to detection of a stabilized ternary complex that contains the respective type of nucleotide, whereas the presence of a cognate of the fourth nucleotide type at a particular position can be imputed based on absence of any signal for ternary complex formation at the position. This embodiment provides the advantage of requiring fewer reagent deliveries than would be required if all four nucleotide types were separately delivered. Another advantage is that this embodiment requires fewer detection channels than would be used if unique signals were distinguished for each of the four nucleotide types. Exemplary embodiments that utilize imputation are set forth in the Examples section below in the context of Tables 1, 2 and 5.

In some embodiments, an SBB™ method is provided that utilizes fewer reagent deliveries and fewer label types than the number of nucleotide types that are distinguished. For example, fewer than three reagent deliveries and fewer than three types of labels can be used in an SBB™ cycle that, nonetheless, provides information to uniquely identify three different base types in a template nucleic acid. As a more specific example, two reagent deliveries and two examinations can be carried out in the following order: (1) the first delivery includes reagents capable of forming a first stabilized ternary complex with a first nucleotide type and a second stabilized ternary complex with a second nucleotide type (e.g. a dGTP-ternary complex and a dCTP-ternary complex); (2) the product of the first delivery is subjected to a first examination; (3) the second delivery includes reagents capable of forming the first stabilized ternary complex with the first nucleotide type and a third stabilized ternary complex with a third nucleotide type (e.g. dGTP-ternary complex and a dTTP-ternary complex); and (4) the product of the second delivery is subjected to a second examination. The different ternary complexes can be labeled in any of a variety of ways but the labels need not distinguish one type of ternary complex from another. In other words, any signals detected in the above examination steps can be ambiguous with respect to the type of nucleotide that participated in ternary complex formation. The results of the second examination can be used to disambiguate the results of the first examination and vice versa. More specifically disambiguation can be achieved by a comparison where: dGTP is identified from the presence of signal in both the first and second examinations, or dCTP is called from the presence of signal in the first examination and absence of signal in the second examination, or dTTP is called from absence of signal in the first examination and presence of signal in the second examination. Furthermore, in this example, the absence of signal in both examinations can be called as if a dATP had been present, even if it was not. Exemplary embodiments that utilize disambiguation are set forth in the Examples section in the context of Tables 2-5.

A further SBB™ embodiment can employ label switching for one or more nucleotide type in alternate reagent delivery steps. As such, the change in signal that is detected for the same type of stabilized ternary complex can be used as a basis for disambiguating the identity of the nucleotide in the ternary complex. More specifically, different types of stabilized ternary complexes can produce a different combination of signal states when multiple different reagent deliveries are compared. The unique combination of signal states across multiple reagent deliveries provides a signature (also referred to herein as a 'codeword') that uniquely identifies different base types in a template nucleic acid. Exemplary embodiments that utilize alternating signal states as a unique signature are set forth in the Examples section in the context of Tables 3, 4, 5, 7 and 8.

As will be apparent from the above example, methods set forth herein can provide the advantage of reducing the complexity and cost of detection hardware and can also provide the advantage of reducing cycle time and reagent cost compared to previous SBB™ methods.

Particular embodiments of the present disclosure provide improved accuracy. Using methods set forth herein, ternary complexes can be formed and examined multiple times at a particular position in a primed template. In a sequencing method, this can be achieved by performing a cycle that includes multiple reagent deliveries and examination steps for a particular position in a primed template prior to advancing to the next cycle by extending the primer. This can effectively result in serial or repetitive examinations of a particular cognate nucleotide type at a given template position. These serial or repetitive examinations can be combined to provide a more accurate nucleotide call than would be available from a single examination of the particular cognate nucleotide type at that position. Moreover, serial or repetitive examinations of this type can provide statistical analysis or variance measures for nucleotides called at individual positions in a primed template. Such information can in turn be used to evaluate overall accuracy for a sequence determination.

Repetitive examinations can be achieved by merely repeating steps within a typical SBB™ cycle. For example, the repeated steps can involve delivering reagents to form four uniquely labeled types of ternary complexes and examining the ternary complexes using detectors that distinguish the different types of ternary complexes in a mixture. As another example, the repeated steps can involve separately delivering reagents to form each of four different types of ternary complexes and separately detecting the product of each delivery. The former configuration has a relative disadvantage of requiring more complex detection hardware and the latter configuration has a relative disadvantage of consuming relatively more time and reagents. In accordance with disambiguation methods set forth herein, a position in a primed template can be sequentially treated with different mixtures of reagents for forming ternary complexes and the resulting mixtures can be examined. Appropriate selection of nucleotide types across combinatorial mixtures can allow the position to be treated and examined fewer times and/or with fewer label types than would be required when merely using repetitive delivery of the same reagents. Exemplary embodiments that utilize disambiguation and provide improved accuracy are set forth in the Examples section in the context of Tables 3, 9 and 10.

Particular embodiments of the methods set forth herein utilize an encoding scheme that provides for error detection and error correction. Serial examinations produce a series of signal states, respectively. For example, different types of ternary complexes can be labeled with different colored luminophores and the series of colors emitted from the series of examinations can encode the type of nucleotide that is present at the position of the template nucleic acid where the series of ternary complexes formed. Each different nucleotide type is encoded by a unique series of signal states. For sake of explanation, the code can be represented as a series of digits that form a codeword of length n, wherein each digit represents a signal state (e.g. a first color or second color in the case of a binary digit based on luminescence color) and the length of the codeword is the same as the number of examinations. Error detection is possible when the number of possible codewords exceeds the number of expected nucleotide types. More specifically, error detection is provided since a base call can be identified as valid when it is derived from a codeword that is expected for one of the nucleotide types or invalid when it is derived from a codeword that is not assigned to any nucleotide type. Moreover, error correction can be provided by an appropriate selection of code complexity and distance between codes for valid base calls. For example, the codewords for each valid base call can differ from the codewords for all other valid base calls by at least three digits. As a consequence, up to two errors per codeword can be detected while a single error can be corrected. Any of a variety of error detecting or error correcting codes used in telecommunications, information theory or coding theory can be adapted for use in a method set forth herein, including but not limited to, a repetition code, parity code, error detecting code, error correcting code, linear code or Hamming code. Exemplary embodiments that utilize error detecting codes are set forth in Example 8 and exemplary embodiments that utilize error correcting codes are set forth in Example 9.

In sequencing embodiments it may be beneficial to change the examination technique for different cycles. For example, in situations where later sequencing cycles are expected to be more error prone than earlier cycles, it may be beneficial to increase the number of examination steps per cycle as sequencing proceeds. It may be beneficial to use a relatively low number of examination steps and/or fewer labels during early sequencing cycles, to minimize reagent costs and sequencing time, and then the number of examination steps and/or labels can be increased during later cycles to improve accuracy. Accordingly, error detection codes or error correction codes can be used at later cycles in a sequencing protocol even if they are not used in the early cycles. Any of the multiple examination and/or encoding schemes set forth herein can be initiated after 10, 25, 50, 100, 200, 500 or more cycles of a sequencing technique.

A variety of SBB™ techniques can be modified in accordance with the teachings set forth herein including, for example, those described in commonly owned U.S. Pat. App. Pub. No. 2017/0022553 A1 or U.S. Pat. App. Pub. No. 2018/0044727 A1, which claims priority to U.S. patent application Ser. No. 62/447,319; or U.S. patent application Ser. No. 15/851,383, which claims benefit of U.S. patent application Ser. No. 62/440,624; or U.S. patent application Ser. No. 15/873,343, which claims priority to U.S. patent application Ser. No. 62/450,397, each of which is incorporated herein by reference.

Furthermore, although methods that employ imputation and disambiguation are exemplified herein with regard to sequencing reactions that employ repeated cycles, the cycles need not be repeated. For example, a genotyping method that probes a single nucleotide position in a template nucleic acid via formation of a stabilized ternary complex can be carried out with only a subset of the possible nucleotide types that would be expected to form cognates with the template being genotyped and the identity of the omitted nucleotide can be imputed. In another example fewer than three reagent deliveries and fewer than three types of labels can be used in a genotyping reaction that, nonetheless, provides information to uniquely identify three or four different nucleotide types using disambiguation and/or alternating signal states. The position being probed in a genotyping embodiment can be identified using an encoding scheme that allows error detection or error correction. Examples of genotyping techniques that can be modified to employ imputation and/or disambiguation techniques set forth herein include those set forth in commonly owned U.S. patent application Ser. No. 15/701,373, which claims the benefit of U.S. Provisional App. No. 62/448,630, each of which is incorporated herein by reference.

Terms used herein will be understood to take on their ordinary meaning in the relevant art unless specified otherwise. Several terms used herein and their meanings are set forth below.

As used herein, the term "ambiguous," when used in reference to a signal, means that the signal apparently has more than one potential origin. For example, an ambiguous signal that is acquired in a cycle of a sequencing reaction may not distinguish between two or more nucleotide types that could participate in the cycle to produce the signal. When used in reference to a nucleic acid representation (e.g. a nucleic acid sequence), the term "ambiguous" refers to a position in the nucleic acid representation for which two or more nucleotide types are identified as candidate occupants. An ambiguous position can have, for example, at least 2, 3 or 4 nucleotide types as candidate occupants. Alternatively or additionally, an ambiguous position can have at most 4, 3 or 2 nucleotide types as candidate occupants.

As used herein, the term "array" refers to a population of molecules that are attached to one or more solid-phase substrates such that the molecules at one feature can be distinguished from molecules at other features. An array can include different molecules that are each located at different addressable features on a solid-phase substrate. Alternatively, an array can include separate solid-phase substrates each functioning as a feature that bears a different molecule, wherein the different molecules can be identified according to the locations of the solid-phase substrates on a surface to which the solid-phase substrates are attached, or according to the locations of the solid-phase substrates in a liquid such as a fluid stream. The molecules of the array can be, for example, nucleotides, nucleic acid primers, nucleic acid templates, primed templates, primed nucleic acid templates, primed template nucleic acid, or nucleic acid enzymes such as polymerases, ligases, exonucleases or combinations thereof.

As used herein, the term "binary complex" refers to an intermolecular association between a polymerase and a primed template nucleic acid, exclusive of a nucleotide molecule such as a next correct nucleotide of the primed template nucleic acid.

As used herein, the term "blocking moiety," when used in reference to a nucleotide analog, refers to a part of the nucleotide analog that inhibits or prevents the nucleotide from forming a covalent linkage to a next correct nucleotide (e.g., via the 3'-oxygen of a primer nucleotide) during the incorporation step of a nucleic acid polymerization reaction. The blocking moiety of a "reversible terminator" nucleotide can be removed from the nucleotide analog, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat. Nos. 7,427,673; 7,414,116; 7,057,026; 7,544,794 or 8,034,923; or PCT publications WO 91/06678 or WO 07/123744, each of which is incorporated herein by reference.

As used herein, the term "call," when used in reference to a nucleotide or base, refers to a determination of the type of nucleotide or base that is present at a particular position in a nucleic acid sequence. A call can be associated with a measure of error or confidence. A call of 'N,' 'null,' 'unknown' or the like can be used for a particular position in a sequence when an error is apparent or when confidence is below a given threshold. A call can designate a discrete type of base or nucleotide (e.g. A, C, G, T or U, using the IUPAC single letter code) or a call can designate degeneracy. Taking IUPAC symbols as an example, a single position can be called as R (i.e. A or G), M (i.e. A or C), W (i.e. A or T), S (i.e. C or G), Y (i.e. C or T), K (i.e. G or T), B (i.e. C or G or T), D (i.e. A or G or T), H (i.e. A or C or T), or V (i.e. A or C or G). A call need not be final, for example, being a proposed call based on incomplete or developing information. In some cases, a call can be deemed as valid or invalid based on comparison of empirical data to a reference. For example, when signal data is encoded, a call that is consistent with a predetermined codeword for a particular base type can be identified as a valid call, whereas a call that is not consistent with codewords for any base type can be identified as an invalid call.

As used herein, the term "catalytic metal ion" refers to a metal ion that facilitates phosphodiester bond formation between the 3' oxygen of a nucleic acid (e.g., a primer) and the 5' phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3' oxygen group of a nucleic acid (e.g., a primer) and the 5' phosphate group of an incoming nucleotide.

As used herein, the term "code," means a system of rules to convert information, such as signals obtained from a detection apparatus, into another form or representation, such as a base call or nucleic acid sequence. For example, signals that are produced by one or more ternary complex having a particular type of bound nucleotide can be encoded by a digit. The digit can have several potential values, each value encoding a different signal state. For example, a binary digit will have a first value for a first signal state and a second value for a second signal state. A digit can have a higher radix including, for example, a ternary digit having three potential values, a quaternary digit having four potential values etc. A series of digits can form a codeword. For example, the series of digits can encode a series of signal states acquired from a series of ternary complex examination steps. The length of the codeword is the same as the number of examination steps performed. Exemplary codes include, but are not limited to, a repetition code, parity code, error detecting code, error correcting code, linear code or Hamming code.

As used herein, the term "comprising" is intended to be open-ended, including not only the recited elements, but further encompassing any additional elements.

As used herein, the term "destabilize" means to cause something to be unable to continue existing or working in a particular way. "Destabilizing" a binary complex refers to the process of promoting dissolution or breakdown of the binary complex. "Destabilizing" also includes the process of inhibiting or preventing formation of the binary complex.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report.

As used herein, the term "disambiguate," when used in reference to nucleotide identity, means identifying a single nucleotide type from a signal that is ambiguous for at least two candidate nucleotide types, the single nucleotide type being one of the candidate nucleotide types.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "error correcting code" means a code that identifies information as being valid or invalid and that further provides recovery of valid information. For example, an error correcting code can have sufficient information to recover valid signals from invalid signals or to make a valid base call from invalid or erroneous signals. An error correcting code can function as an error detecting code.

As used herein, the term "error detecting code" means a code that identifies information as being valid or invalid. For example, an error detecting code can have sufficient information to distinguish valid signals from invalid signals or to distinguish a valid base call from an invalid base call.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide.

Similarly, an exogenous label that is present on a polymerase is not found on the polymerase in its native milieu.

As used herein, the term "extension," when used in reference to a nucleic acid, refers to a process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "feature," when used in reference to an array, means a location in an array where a particular molecule is present. A feature can contain only a single molecule or it can contain a population of several molecules of the same species (i.e. an ensemble of the molecules). Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 micron, 50 micron, 10 micron, 5 micron, 1 micron, or 0.5 micron. Alternatively or additionally, an array can have features that are separated by greater than 0.5 micron, 1 micron, 5 micron, 10 micron, 50 micron or 100 micron. The features can each have an area of less than 1 square millimeter, 500 square micron, 100 square micron, 25 square micron, 1 square micron or less.

As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

As used herein, the term "impute," when used in reference to nucleotide identity, means inferring the presence of a particular type of nucleotide at a position in the nucleic acid absent observation of a detectable event attributable to the nucleotide. For example, the presence of a first nucleotide type at a position in a nucleic acid can be imputed based on absence of an observed signal for the first nucleotide type. Optionally, the imputation of the first nucleotide type's presence at the position can be further influenced by the observation of signal(s) for one or more other nucleotide type at the position.

As used herein, the term "label" means a molecule or moiety thereof that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, the term "mixture," when used in reference to multiple nucleotide types, means a combination of two or more nucleotide types that are simultaneously together, for example, in a liquid or on a surface or as a combination thereof. An exemplary combination is a surface bound reaction component that is in contact with a solution phase component. A mixture can be distinguished from a chemical compound in that the two or more different things need not necessarily be in fixed proportions, need not lose their individual characteristics, and/or can be separated by physical means.

As used herein, the term "next correct nucleotide" refers to the nucleotide type that will bind and/or incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be referred to as the "cognate" of the next template nucleotide and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide. A "nucleotide cognate" of a specified base type (e.g., a nucleotide cognate of a first base type, a nucleotide cognate of a second base type, a nucleotide cognate of a third base type, or a nucleotide cognate of a fourth base type) is a nucleotide that is complementary to, and/or capable of selectively pairing with, the specified base type (e.g., preferentially pairing with a single specified base type over all other candidate base types in a template strand). For example, a nucleotide cognate of a first base type (e.g., of four possible types) is complementary to, and/or capable of pairing with, a first base type and not a different base type (e.g., a second, third, or fourth base type). Likewise, for example, a nucleotide cognate of a second base type (e.g., of four possible types) is complementary to, and/or capable of pairing with, a second base type not a different base type (e.g., a first, third, or fourth base type). A nucleotide cognate may or may not be the next correct nucleotide. Thus, in some embodiments a nucleotide cognate is a next correct nucleotide (i.e., the nucleotide is capable of pairing to the base type of the next template nucleotide). In alternative embodiments, a nucleotide cognate is not a next correct nucleotide (i.e., the nucleotide is not capable of pairing to the base type of the next template nucleotide, but instead pairs with another type of nucleotide that is not present at the next template nucleotide position). In embodiments, a nucleotide cognate of a first, second, third, or fourth base type is capable of pairing with a first, second, third, or fourth base type, respectively, and not one of the three other base types. In embodiments, the first second, third, and fourth base types are, respectively, A, C, G, T; A, C, T, G; A, G, C, T; A, G, T, C; A, T, C, G; A, T, G, C; C, G, T, A; C, G, A, T; C, T, G, A; C, T, A, G; C, A, G, C; C, A, C, G; G, T, A, C; G, T, C, A; G, A, C, T; G, A, T, C; G, C, T, A; G, C, A, T; C, G, T, A; C, G, A, T; C, T, G, A; C, T, A, G; C, A, G, T; or C, A, T, G, all being commonly used single letter labels for DNA base types. In embodiments, the first second, third, and fourth base types are, respectively, A, C, G, U; A, C, U, G; A, G, C, U; A, G, U, C; A, U, C, G; A, U, G, C; C, G, U, A; C, G, A, U; C, U, G, A; C, U, A, G; C, A, G, C; C, A, C, G; G, U, A, C; G, U, C, A; G, A, C, U; G, A, U, C; G, C, U, A; G, C, A, U; C, G, U, A; C, G, A, U; C, U, G, A; C, U, A, G; C, A, G, U; or C, A, U, G As used herein, the term "non-catalytic metal ion" refers to a metal ion that, when in the presence of a polymerase enzyme, does not facilitate phosphodiester bond formation needed for covalent incorporation of a nucleotide into a primer. A non-catalytic metal ion may interact with a polymerase, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "primed template," "primed template nucleic acid," or "primed nucleic acid template" refers to a nucleic acid hybrid having a double stranded region such that one of the strands has a 3'-end that can be extended by a polymerase (e.g., by covalently attaching a next correct nucleotide to the 3'-end of the strand), optionally following deblocking of the strand to be extended by the polymerase. The two strands can be parts of a contiguous nucleic acid molecule (e.g. a hairpin structure) or the two strands can be separable molecules that are not covalently attached to each other.

As used herein, the term "primer" means a nucleic acid having a sequence that binds (e.g., is complementary) to a nucleic acid at or near a template sequence. Generally, the primer binds in a configuration that allows replication of the template, for example, via polymerase extension of the primer (e.g., the primer may need to be deblocked prior to replication). In embodiments, when hybridized to a template sequence, the primer is capable of binding a polymerase (e.g. thereby allowing for primer extension). The primer may be of any appropriate length. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof.

As used herein, the term "signal" refers to energy or coded information that can be selectively observed over other energy or information such as background energy or information. A signal can have a desired or predefined characteristic. For example, an optical signal can be characterized or observed by one or more of intensity, wavelength, energy, frequency, power, luminance or the like. Other signals can be quantified according to characteristics such as voltage, current, electric field strength, magnetic field strength, frequency, power, temperature, etc. An optical signal can be detected at a particular intensity, wavelength, or color; an electrical signal can be detected at a particular frequency, power or field strength; or other signals can be detected based on characteristics known in the art pertaining to spectroscopy and analytical detection. Absence of signal is understood to be a signal level of zero or a signal level that is not meaningfully distinguished from noise.

As used herein, the term "signal state" refers to a mode or characteristic of a signal obtained from a detector. Exemplary modes or characteristics include, but are not limited to, wavelength of energy absorption, wavelength of luminescent excitation, wavelength of luminescence emission, intensity of energy absorption, intensity of luminescent excitation, intensity of luminescent emission, polarization state, luminescence lifetime, color. A signal state can have multiple potential values. For example, a signal state can have two potential states (binary), three potential states (ternary), four potential states (quaternary) etc. An example of a binary signal state is presence or absence of signal detected at a particular wavelength. Another example of a binary signal state is luminescence emission detected at a first wavelength or second wavelength.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, the term "type" is used to identify molecules that share the same chemical structure. For example, a mixture of nucleotides can include several dCTP molecules. The dCTP molecules will be understood to be the same type as each other, but a different type compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

The embodiments set forth below and recited in the claims can be understood in view of the above definitions.

The present disclosure provides methods for identifying the base type at one or more positions of a nucleic acid. A reaction can be carried out to form a stabilized ternary complex, between a primed template nucleic acid, a polymerase and a next correct nucleotide, wherein only a subset of the possible nucleotide types that are candidates for forming cognates with bases in the template are present or detectable. The identities of nucleotides in the subset of nucleotides can be determined from detected signals whereas a nucleotide that does not participate in the reaction (or at least does not produce a detected signal in the reaction) can be identified by imputation. It will be understood that, in accordance with Watson-Crick base-pairing rules, the identity of a cognate base at a position in a nucleic acid can be readily determined from the identity of the type of nucleotide that is present in a stabilized ternary complex formed at the position.

In some embodiments, the subset of possible nucleotide types can be simultaneously present in a ternary complex forming reaction. Accordingly, this disclosure provides a method of nucleic acid detection, that includes the steps of (a) forming a mixture under ternary complex stabilizing conditions, wherein the mixture includes a primed template nucleic acid, a polymerase and nucleotide cognates of first, second and third base types in the template; (b) examining the mixture to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

Alternatively, different nucleotide types in a subset of candidates can be serially reacted with a template nucleic acid under conditions to form ternary complex with a polymerase. Accordingly, the present disclosure provides a method of nucleic acid detection that includes the steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

Described herein are polymerase-based methods for detecting nucleic acids. Embodiments of the methods exploit the specificity with which a polymerase can form a stabilized ternary complex with a primed template nucleic acid and a next correct nucleotide. In particular embodiments, the next correct nucleotide is non-covalently bound to the stabilized ternary complex, interacting with the other members of the complex solely via non-covalent interactions. Useful methods and compositions for forming a stabilized ternary complex are set forth in further detail below and in commonly owned U.S. Pat. App. Pub. No. 2017/0022553 A1 or U.S. Pat. App. Pub. No. 2018/0044727 A1, which claims priority to U.S. patent application Ser. No. 62/447,319; or U.S. patent application Ser. No. 15/851,383, which claims benefit of U.S. patent application Ser. No. 62/440,624; or U.S. patent application Ser. No. 15/873,343, which claims priority to U.S. patent application Ser. No. 62/450,397, each of which is incorporated herein by reference.

While a ternary complex can form between a polymerase, primed template nucleic acid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, causes non-covalent sequestration of the next correct nucleotide in a stabilized ternary complex. Other methods disclosed herein also can be used to produce a stabilized ternary complex.

Optionally, a stabilized ternary complex can be formed when the primer of the primed template nucleic acid includes a blocking moiety (e.g. a reversible terminator moiety) that precludes enzymatic incorporation of an incoming nucleotide into the primer. The interaction can take place in the presence of stabilizers, whereby the polymerase-nucleic acid interaction is stabilized in the presence of the next correct nucleotide (i.e., stabilizers that stabilize the ternary complex). The primer of the primed template nucleic acid optionally can be either an extendible primer, or a primer blocked from extension at its 3'-end (e.g., by the presence of a reversible terminator moiety). The primed template nucleic acid, the polymerase and the cognate nucleotide are capable of forming a stabilized ternary complex when the base of the cognate nucleotide is complementary to the next base of the primed template nucleic acid (e.g., the next template nucleotide).

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide (e.g., next correct nucleotide)) are provided by the presence of one or more monovalent cations and/or glutamate anions. As a further option, a polymerase engineered to have reduced catalytic activity or reduced propensity for binary complex formation can be used.

As set forth above, ternary complex stabilization conditions can accentuate the difference in affinity of polymerase toward primed template nucleic acids in the presence of different nucleotides, for example, by destabilizing binary complexes. Optionally, the conditions cause differential affinity of the polymerase for the primed template nucleic acid in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate ions. Optionally, the source of glutamate ions can be potassium glutamate. In some instances, the concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 to 1,500 mM salt.

It will be understood that options set forth herein for stabilizing a ternary complex need not be mutually exclusive and instead can be used in various combinations. For example, a ternary complex can be stabilized by one or a combination of means including, but not limited to, cross-linking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, presence of a blocking moiety on the primer, and other means set forth herein.

A stabilized ternary complex can include a native nucleotide, nucleotide analog or modified nucleotide as desired to suit a particular application or configuration of the methods. Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Examples of nucleotide analogs are described in U.S. Pat. No. 8,071,755, which is incorporated by reference herein.

Nucleotide analogs that participate in stabilized ternary complexes can include terminators that reversibly prevent nucleotide incorporation at the 3'-end of the primer after the analog has been incorporated. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in references cited previously herein or in U.S. Pat. Nos. 7,956,171, 8,071,755, and 9,399,798 (the disclosures of these U.S. patents are incorporated herein by reference). In certain embodiments, a reversible blocking moiety can be removed from a primer, in a process known as "deblocking," allowing for subsequent nucleotide incorporation. Compositions and methods for deblocking are set forth in references cited herein in the context of reversible terminators.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Irreversibly terminated nucleotides can be particularly useful for genotyping applications.

In some embodiments, a nucleotide that participates in forming a ternary complex can include an exogenous label. For example, an exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. Exogenously labelled nucleotides can be particularly useful when used to form a stabilized ternary complex with a non-labelled polymerase. Alternatively, an exogenous label on a nucleotide can provide one partner in a fluorescence resonance energy transfer (FRET) pair and an exogenous label on a polymerase can provide the second partner of the pair. As such, FRET detection can be used to identify a stabilized ternary complex that includes both partners. Alternatively, a nucleotide that participates in forming a ternary complex can lack exogenous labels (i.e. the nucleotide can be "non-labeled"). For example, a non-labeled nucleotide can include a reversible or irreversible terminator moiety, a non-labeled nucleotide can be non-incorporable, a non-labeled nucleotide can lack terminator moieties, a non-labeled nucleotide can be incorporable or a non-labeled labeled nucleotide can be both incorporable and non-terminated. Non-labelled nucleotides can be useful when a label on a polymerase is used to detect a stabilized ternary complex. Non-labelled nucleotides can also be useful in an extension step of an SBB™ method. It will be understood that absence of a moiety or function for a nucleotide refers to the nucleotide having no such function or moiety. However, it will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or nucleotide analog) is present in a mixture during formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid.

Any nucleotide modification that stabilizes a polymerase in a ternary complex may be used in the methods disclosed herein. The nucleotide may be bound permanently or transiently to a polymerase. Optionally, a nucleotide analog is fused to a polymerase, for example, via a covalent linker. Optionally, a plurality of nucleotide analogs are fused to a plurality of polymerases, wherein each nucleotide analog is fused to a different polymerase. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primed template nucleic acid molecule that is present in a stabilized ternary complex is chemically unchanged by the polymerase that is present during one or more steps of a method set forth herein. For example, the primer need not be extended by formation of a new phosphodiester bond, nor shortened by nucleolytic degradation during a step for forming a stabilized ternary complex, nor during a step for examining the stabilized ternary complex.

Any of a variety of polymerases can be used to form a stabilized ternary complex in a method set forth herein. Polymerases that may be used include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction in at least one condition that is not used during formation or examination of a stabilized ternary complex. Optionally, the naturally-occurring and/or modified variations that participate in stabilized ternary complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques. For example, the exogenous label moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET.

Alternatively, a polymerase that participates in a stabilized ternary complex need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

A ternary complex that is made or used in accordance with the present disclosure may optionally include one or more exogenous label(s). The label can be attached to a component of the ternary complex (e.g. attached to the polymerase, template nucleic acid, primer and/or cognate nucleotide) prior to formation of the ternary complex. Exemplary attachments include covalent attachments or non-covalent attachments such as those set forth herein, in references cited herein or known in the art. In some embodiments, a labeled component is delivered in solution to a solid support that is attached to an unlabeled component, whereby the label is recruited to the solid support by virtue of forming a stabilized ternary complex. As such, the support-attached component can be detected or identified based on observation of the recruited label. Whether used in solution phase or on a solid support, exogenous labels can be useful for detecting a stabilized ternary complex or an individual component thereof, during an examination step. An exogenous label can remain attached to a component after the component dissociates from other components that had formed a stabilized ternary complex. Exemplary labels, methods for attaching labels and methods for using labeled components are set forth in commonly owned U.S. Pat. App. Pub. No. 2017/0022553 A1 or U.S. Pat. App. Pub. No. 2018/0044727 A1, which claims priority to U.S. patent application Ser. No. 62/447,319; or U.S. patent application Ser. No. 15/851,383, which claims benefit of U.S. patent application Ser. No. 62/440,624; or U.S. patent application Ser. No. 15/873,343, which claims priority to U.S. patent application Ser. No. 62/450,397, each of which is incorporated herein by reference.

Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore moieties include, but are not limited to umbelliferone, fluorescein, isothiocyanate, rhodamine, tetramethyl rhodamine, eosin, green fluorescent protein, erythrosin, coumarin, methyl coumarin, pyrene, malachite green, stilbene, *lucifer* Yellow™, Cascade Blue™, Texas Red™, dansyl chloride, phycoerythrin, phycocyanin, fluorescent lanthanide complexes such as those including Europium and Terbium, Cy3, Cy5, and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

It will be understood that in some embodiments a particular signal characteristic can be detected from different labels. In other words, labels having different chemical structures can be used for purposes of producing a similar signal state. The use if different labels can be advantageous for optimizing chemical behavior while achieving a desired detection capability. For example, an examination step can observe an ensemble of ternary complexes formed by a mixture of nucleotide analogs, wherein the nucleotide analogs all include the same base type but individual analogs in the mixture have different labels. The nucleotide mixture can include labels that all emit luminescence at a desired wavelength, but the distribution of labels in the mixture can be selected to optimize the average binding affinity of the mixture for the polymerase. Thus, a method set forth herein can detect the same signal state from different labels having a common signal producing characteristic.

A secondary label can be used in a method of the present disclosure. A secondary label is a binding moiety that can bind specifically to a labeled partner moiety. For example, a ligand moiety can be attached to a polymerase, nucleic acid or nucleotide to allow detection via specific affinity for labeled receptor. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins.

In some embodiments, the secondary label can be a chemically modifiable moiety. In this embodiment, labels having reactive functional groups can be incorporated into a stabilized ternary complex. Subsequently, the functional group can be covalently reacted with a primary label moiety.

Suitable functional groups include, but are not limited to, amino groups, carboxy groups, maleimide groups, oxo groups and thiol groups.

In alternative embodiments, a ternary complex can lack exogenous labels. For example, a ternary complex and all components participating in the ternary complex (e.g. polymerase, template nucleic acid, primer and/or cognate nucleotide) can lack one, several or all of the exogenous labels described herein or in the above-incorporated references. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916 (published as WO 2017/117243), or U.S. Pat. App. Pub. No. 2018/0044727 A1, which claims priority to U.S. patent application Ser. No. 62/375,379, each of which is incorporated herein by reference.

A method of the present disclosure can include an examination step. Generally, detection can be achieved in an examination step by methods that perceive a property that is intrinsic to a ternary complex or a label moiety attached thereto. Exemplary properties upon which detection can be based include, but are not limited to, mass, electrical conductivity, energy absorbance, luminescence (e.g. fluorescence) or the like. Detection of luminescence can be carried out using methods known in the art pertaining to nucleic acid arrays. A luminophore can be detected based on any of a variety of luminescence properties including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Examples of reagents and conditions that can be used to create, manipulate and detect stabilized ternary complexes include, for example, those set forth in commonly owned U.S. Pat. App. Pub. No. 2017/0022553 A1; PCT App. Ser. No. PCT/US16/68916 (published as WO 2017/117243); or U.S. Pat. App. Pub. No. 2018/0044727 A1, which claims priority to U.S. patent application Ser. No. 62/447,319; or U.S. patent application Ser. No. 15/851,383, which claims benefit of U.S. patent application Ser. No. 62/440,624; or U.S. patent application Ser. No. 15/873,343, which claims priority to U.S. patent application Ser. No. 62/450,397, each of which is incorporated herein by reference.

In particular embodiments, signal is not detected for stabilized ternary complex formed with a particular nucleotide type and the identity of the nucleotide is imputed. In such embodiments, a primed template nucleic acid need not be contacted with that particular nucleotide during any or all examination or detection steps of the method. Alternatively, the particular nucleotide can be present during an examination step, but undetectable under the conditions employed. For example, the nucleotide may form a stabilized ternary complex that is not detectable. The lack of detectability may derive from absence of an exogenous label on the nucleotide or on the polymerase that it binds to in the stabilized ternary complex, or the lack of detectability may derive from use of a detection condition that is not configured to detect a label that is present on the nucleotide or on the polymerase that it binds to in the stabilized ternary complex. As set forth in further detail below, one or more nucleotide types that are not present during an examination step can nevertheless be provided during an extension step.

It may be advantageous to include all four different types of nucleotides in a mixture even though the mixture will be examined for only a subset of ternary complex types. For example, the mixture can include nucleotides having all four base types, wherein a first subset of the nucleotides (e.g. A and G) have a label that is detected and a second subset of the nucleotides (e.g. C and T) do not have the label that is detected. The presence of all four nucleotide types in a mixture can help prevent formation of ternary complexes having non-cognate nucleotides because correct nucleotides will be present to out compete incorrect nucleotides in the binding mixture. Thus, the presence of all four nucleotide types can favor formation of ternary complexes having correctly bound cognate nucleotides to improve accuracy of sequencing results.

Particular embodiments of the methods set forth herein include a step of forming a mixture that includes several components. For example, a mixture can be formed between a primed template nucleic acid, a polymerase and one or more nucleotide types. The components of the mixture can be delivered to a vessel in any desired order or they can be delivered simultaneously. Furthermore, some of the components can be mixed with each other to form a first mixture that is subsequently contacted with other components to form a more complex mixture. Taking as an example, a step of forming a mixture that includes a primed template nucleic acid, a polymerase and a plurality of different nucleotide types, it will be understood that the different nucleotide types in the plurality can be contacted with each other prior to being contacted with the primed template nucleic acid. Alternatively, two or more of the nucleotide types can be delivered separately to the primed template nucleic acid and/or the polymerase. As such, a first nucleotide type can be contacted with the primed template nucleic acid prior to being contacted with a second nucleotide type. Alternatively or additionally, the first nucleotide type can be contacted with the polymerase prior to being contacted with a second nucleotide type.

Some embodiments of the methods set forth herein utilize two or more distinguishable signals to distinguish stabilized ternary complexes from each other and/or to distinguish one base type in a template nucleic acid from another base type. For example, two or more luminophores can be distinguished from each other based on unique optical properties such as unique wavelength for excitation or unique wavelength of emission. In particular embodiments, a method can distinguish different stabilized ternary complexes based on differences in luminescence intensity. For example, a first ternary complex can be detected in a condition where it emits less intensity than a second ternary complex. Such intensity scaling (sometimes called 'grey scaling') can exploit any distinguishable intensity difference. Exemplary difference include a particular stabilized ternary complex having an intensity that is 10%, 25%, 33%, 50%, 66%, or 75% compared to the intensity of another stabilized ternary complex that is to be detected.

Intensity differences can be achieved using different luminophores each having a different extinction coefficient (i.e. resulting in different excitation properties) and/or different luminescence quantum yield (i.e. resulting in different emission properties). Alternatively, the same luminophore type can be used but can be present in different amounts. For example, all members of a first population of ternary complexes can be labeled with a particular luminophore, whereas a second population has only half of its members labeled with the luminophore. In this example, the second population would be expected to produce half the signal of the first population. The second population can be produced, for example, by using a mixture of labeled nucleotides and unlabeled nucleotides (in contrast to the first population containing primarily labeled nucleotides). Similarly, the second population can be produced, for example, by using a mixture of labeled polymerases and unlabeled polymerases (in contrast to the first population containing primarily labeled polymerases). In an alternative labeling scheme, a first population of ternary complexes can include polymerase molecules that have multiple labels that produce a particular luminescent signal and a second population of ternary complexes can include polymerase molecules that each have only one of the labels that produces the luminescent signal.

The present disclosure provides a method of nucleic acid detection that includes the steps of (a) contacting a primed template nucleic acid with a polymerase and a first mixture of nucleotides under ternary complex stabilizing conditions, wherein the first mixture includes a nucleotide cognate of a first base type and a nucleotide cognate of a second base type; (b) contacting the primed template nucleic acid with a polymerase and a second mixture of nucleotides under ternary complex stabilizing conditions, wherein the second mixture includes a nucleotide cognate of the first base type and a nucleotide cognate of a third base type; (c) examining products of steps (a) and (b) for signals produced by a ternary complex that includes the primed template nucleic acid, a polymerase and a next correct nucleotide, wherein signals acquired for the product of step (a) are ambiguous for the first and second base type, and wherein signals acquired for the product of step (b) are ambiguous for the first and third base type; (d) disambiguating signals acquired in step (c) to identify a base type that binds the next correct nucleotide. Optionally, to achieve disambiguation (i) the first base type is correlated with presence of signals for the product of step (a) and presence of signals for the product of step (b), (ii) the second base type is correlated with presence of signals for the product of step (a) and absence of signals for the product of step (b), and (iii) the third base type is correlated with absence of signals for the product of step (a) and presence of signals for the product of step (b).

Also provided is a method of nucleic acid detection that includes the steps of (a) contacting a primed template nucleic acid with a first mixture including a polymerase, a nucleotide cognate of a first base type in the template and a nucleotide cognate of a second base type in the template, wherein the contact occurs in a binding reaction that (i) stabilizes ternary complexes including the primed template nucleic acid, the polymerase and a next correct nucleotide, and (ii) prevents incorporation of the next correct nucleotide into the primer; (b) examining the binding reaction to determine whether a ternary complex formed; (c) subjecting the primed template nucleic acid to a repetition of steps (a) and (b), wherein the first mixture is replaced with a second mixture, the second mixture including a polymerase, a nucleotide cognate of the first base type in the template and a nucleotide cognate of a third base type in the template; and (d) identifying the next correct nucleotide for the primed template nucleic acid using the examination of the binding reactions, or a product thereof, wherein (i) the next correct nucleotide is identified as a cognate of the first base type if ternary complex is detected in step (b) and detected in the repetition of step (b), (ii) the next correct nucleotide is identified as a cognate of the second base type if ternary complex is detected in step (b) and undetected in the repetition of step (b), and (iii) the next correct nucleotide is identified as a cognate of the third base type if ternary complex is undetected in step (b) and detected in the repetition of step (b).

In particular embodiments, a primed template nucleic acid can be contacted with two or more mixtures under ternary complex stabilizing conditions. The primed template nucleic acid can be sequentially contacted with the mixtures. For example, a primed template nucleic acid can be contacted with a polymerase and nucleotides under ternary complex stabilization conditions and then the polymerase can be replaced with another polymerase under ternary complex stabilization conditions. Alternatively or additionally, one or more of the nucleotides can be replaced with one or more other nucleotides under ternary complex stabilizing conditions. In some embodiments, the polymerase and all of the nucleotides of the first mixture are replaced with another polymerase and other nucleotides. In an alternative embodiment, two or more mixtures can be in simultaneous contact with a primed template nucleic acid under ternary complex stabilizing conditions.

In many embodiments, a primed template nucleic acid can be contacted with two or more mixtures under ternary complex stabilizing conditions, wherein the first mixture is formed with the primed template nucleic acid and at least one nucleotide type that differs from at least one nucleotide type present in the second mixture. In such cases, the same type of polymerase can be present in both the first and second mixtures, either because the polymerase is not removed from the first mixture when the second mixture is formed or because the polymerase is removed from the first mixture and replaced with a polymerase of the same type. It is also possible to replace the polymerase of a first mixture with a polymerase of a different type when forming the second mixture. Polymerase replacement can be used, for example, to exploit different properties or activities. For example, a first mixture can include a first nucleotide type and a first polymerase having relatively high affinity or specificity for the first nucleotide type, and the second mixture can have a second nucleotide type and a second polymerase having relatively high affinity or specificity for the second nucleotide type. In this example, the first polymerase can have higher affinity or specificity for the first nucleotide compared to the second nucleotide type. Alternatively or additionally, the second polymerase can have higher affinity or specificity for the second nucleotide type compared to the first nucleotide type. In another example, it may be desirable for the second mixture to include a polymerase that is more conveniently converted from a ternary complex stabilized state to a primer extending state (as compared to the polymerase used to form the first ternary complex).

In embodiments where a primed template nucleic acid is sequentially contacted with two or more polymerase-nucleotide mixtures under ternary complex stabilizing conditions, examination can be carried out after each sequential contact. For example, the primed template nucleic acid can be contacted with a polymerase and nucleotide to form a first mixture, then the first mixture can be examined for ternary complex formation, then the primed template nucleic acid can be contacted with a polymerase and a nucleotide to form a second mixture, and then the second mixture can be examined for ternary complex formation. Alternatively, two or more mixtures can be formed prior to carrying out an examination step. As such, examination need not intervene two or more sequential steps of contacting a primed template nucleic acid with reagents for forming stabilized ternary complexes.

One or more wash steps can be useful for separating a primed template nucleic acid from other reagents that were contacted with the primed template nucleic acid under ternary complex stabilizing conditions. Such a wash can remove one or more reagents from interfering with examination of a mixture or from contaminating a second mixture that is to be formed on a substrate (or in a vessel) that had previously been in contact with the first mixture. For example, a primed template nucleic acid can be contacted with a polymerase and at least one nucleotide type to form a first mixture under ternary complex stabilizing conditions, and the first mixture can be examined. Optionally, a wash can be carried out prior to examination to remove reagents that are not participating in formation of a stabilized ternary complex. Alternatively or additionally, a wash can be carried out after the examination step to remove one or more component of the first mixture from the primed template nucleic acid. Then the primed template nucleic acid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex.

A method set forth herein, can include a step of examining a mixture that includes a primed template nucleic acid, polymerase, nucleotide cognate of a first base type in the template and nucleotide cognate of a second base type in the template, wherein signals acquired from the mixture are ambiguous for the first and second base type. The ambiguity can arise, for example, when signals are acquired from an exogenous label attached to the polymerase, such that the signals do not distinguish which nucleotide type is present in a stabilized ternary complex that is detected via the label. Ambiguity can arise when the nucleotides in the mixture do not have exogenous labels or when the different nucleotides do not have unique labels. For example, when two or more nucleotides in a mixture are attached to the same type of exogenous label (or to different exogenous labels that produce an overlapping signal) a signal arising from the mixture, although indicating presence of a ternary complex, may not provide adequate information to distinguish a ternary complex having one of the nucleotides from a ternary complex having the other nucleotide. However, in some embodiments that produce ambiguous signal, the identity of the nucleotides can be disambiguated by examining the same primed template nucleic acid in the presence of a second mixture under ternary complex stabilizing conditions. Specifically, the second mixture can lack one of the nucleotide types that was in the first mixture. The nucleotide type that was present in both mixtures can be identified based on the fact that signal was detected in both mixtures, whereas a nucleotide type that was present in a first mixture and not the second mixture can be identified based on presence of signal in the first mixture and lack of signal in the second mixture. Several specific examples, that utilize disambiguation are set forth in the Examples below (see Tables 2-5). A particularly useful disambiguation method utilizes an encoding scheme, whereby the series of signals detected from the series of mixtures produces a codeword, and the codeword is decoded to make a base call. Exemplary embodiments that use a codeword for disambiguation are set forth below in Examples 8 and 9.

An advantage of the disambiguation methods set forth herein is that the number of different nucleotide types that are uniquely identified can surpass the number of unique signals detected (or the number of labels used). For example, two or more nucleotide types can be distinguished in a method set forth herein based on detection of a signal that is common to both. By way of further example, signals from a first mixture having a primed template nucleic acid, polymerase and two or more nucleotides can be acquired by a detector that is also used to detect signals from a second mixture having the primed template nucleic acid, a polymerase and two or more nucleotides. In this example, the first mixture can include a nucleotide cognate of a first base type and a nucleotide cognate of a second base type, whereas the second mixture can include a nucleotide cognate of the first base type and a nucleotide cognate of a third base type. As a further option in this example, signals acquired for the first mixture can be ambiguous for the first and second base type, and signals acquired for the second mixture can be ambiguous for the first and third base type.

As exemplified by several embodiments set forth herein, three base types at a particular position of a primed template nucleic acid can be distinguished using as few as two binding reactions and as few as one type of label. In such embodiments, the first binding reaction includes a first and second nucleotide type, and the second binding reaction includes the first nucleotide type and a third nucleotide type. The end result is that the first nucleotide type is determined when signal is observed from stabilized ternary complexes formed in both reactions, the second nucleotide type is determined when signal is observed for a ternary complex formed in the first reaction only, and the third nucleotide type is determined when signal is observed for a ternary complex formed in the second reaction only. In this example, the fourth nucleotide type need not participate in a binding reaction with the primed template or, even if the fourth nucleotide is present it need not ever be detected. Rather, the fourth nucleotide can be identified by imputation. More specifically, in the case where the template is a naturally occurring nucleic acid (e.g. genomic DNA or mRNA) it is known that only four types of nucleotides will be present in the template and the absence of signal in both binding reactions can be used to impute that the fourth base type was present at the template position under examination.

As an alternative to imputing the fourth nucleotide type in the above example, a third binding reaction can be performed using the fourth base type and a stabilized ternary complex that includes the fourth base type can be detected. This alternative provides the advantage of confirming the results of the first two binding reactions based on observations of consistent results (e.g. the fourth nucleotide type is observed only in the third binding reaction) or identifying a potential error when inconsistent results are obtained (e.g. the fourth nucleotide type is observed in the third binding reaction and in the first or second binding reaction). This alternative can still provide the advantage of requiring fewer reagent delivery steps than the number of nucleotide types distinguished (i.e. four nucleotide types are distinguished from 3 reagent delivery steps) using as few as one label type.

As demonstrated by the examples set forth herein, four base types can be distinguished at a particular position of a primed template nucleic acid by examining products of a first binding reaction that includes detectable ternary complexes having first and second nucleotide types but lacks detectable ternary complexes having third and fourth nucleotide types, and examining products of a second binding reaction that includes detectable ternary complexes having the first nucleotide type and the third nucleotide type but lacks detectable ternary complexes having second and fourth nucleotide types. A third binding reaction need not be performed nor examined. In this case, speed can be improved and/or costs reduced by employing imputation to identify the fourth nucleotide type. However, if desired, for example, to improve accuracy of sequencing, examination can be carried out for a third binding reaction that includes detectable ternary complexes having only the fourth nucleotide type, or that includes detectable ternary complexes having the fourth nucleotide type along with detectable ternary complexes having one other nucleotide type (but no more than one other nucleotide type).

Generally, accuracy can be improved by repeating reagent delivery and examination steps of a method set forth herein when evaluating a particular position in a primed template nucleic acid. In this way, the position can be tested multiple times for its ability to form a ternary complex with a particular type of nucleotide. Indeed, all four types of nucleotides can be evaluated serially or repetitively for the ability to form ternary complex at a particular position in a primed template. In a Sequencing By Binding embodiment, evaluation can proceed at a subsequent position of the primed template by performing a primer extension step following the serial or repeated examination steps.

Accordingly, this disclosure provides a method of nucleic acid detection that includes steps of (a) sequentially contacting a primed template nucleic acid with at least four separate mixtures under ternary complex stabilizing conditions, wherein each of the mixtures includes a polymerase and nucleotide cognates for at least two of four different base types in the primed template nucleic acid; (b) examining the at least four separate mixtures to detect ternary complexes; and (c) identifying the next correct nucleotide for the primed template nucleic acid molecule, wherein the next correct nucleotide is identified as a cognate of one of the four different base types if ternary complex is detected in at least two of the mixtures.

In an aspect is provided a method of nucleic acid detection that includes steps of (a) sequentially contacting a primed template nucleic acid with at least four separate mixtures under ternary complex stabilizing conditions, wherein each of the mixtures includes a polymerase and nucleotide cognates for at least two of four different base types in the primed template nucleic acid and each of the mixtures includes a different combination of nucleotide cognates for at least two of four different base types in the primed template nucleic acid; (b) examining the at least four separate mixtures to detect ternary complexes; and (c) identifying the next correct nucleotide for the primed template nucleic acid molecule, wherein the next correct nucleotide is identified as a cognate of one of the four different base types if ternary complex is detected in at least two of the mixtures.

Also provided is a method of nucleic acid detection that includes steps of (a) contacting a primed template nucleic acid with a polymerase and a first mixture of nucleotides under conditions for stabilizing a ternary complex at a nucleotide position in the template, wherein the first mixture includes a nucleotide cognate of a first base type and a nucleotide cognate of a second base type; (b) contacting the primed template nucleic acid with a polymerase and a second mixture of nucleotides under conditions for stabilizing a ternary complex at the nucleotide position in the template, wherein the second mixture includes a nucleotide cognate of the first base type and a nucleotide cognate of a third base type; (c) contacting the primed template nucleic acid with a polymerase and a third mixture of nucleotides under conditions for stabilizing a ternary complex at the nucleotide position in the template, wherein the third mixture includes a nucleotide cognate of the second base type and a nucleotide cognate of a fourth base type; (d) contacting the primed template nucleic acid with a polymerase and a fourth mixture of nucleotides under conditions for stabilizing a ternary complex at the nucleotide position in the template, wherein the fourth mixture includes a nucleotide cognate of the third base type and a nucleotide cognate of the fourth base type; (e) examining products of steps (a) through (d) for signals produced by a ternary complex that includes the primed template nucleic acid, a polymerase and a next correct nucleotide, wherein signals acquired for the product of step (a) are ambiguous for the first and second base type, wherein signals acquired for the product of step (b) are ambiguous for the first and third base type, wherein signals acquired for the product of step (c) are ambiguous for the second and fourth base type, and wherein signals acquired for the product of step (d) are ambiguous for the third and fourth base type; (f) disambiguating signals acquired in step (e) to identify a base type that binds the next correct nucleotide.

Particular embodiments of the methods set forth herein use an encoding scheme that can provide for base calling, error detection and even error correction. Different base types can be encoded by series of signal states across several examinations such that decoding the series allows not only for the base to be called but also allows an invalid base call to be identified such that an error can be detected. Error correction is possible for a sufficiently complex encoding scheme.

Accordingly, the present disclosure provides a method of determining a nucleic acid sequence that includes steps of: (a) contacting a primed template nucleic acid with a series of mixtures for forming ternary complexes, wherein each of the mixtures includes a polymerase and nucleotide cognates for at least two different base types suspected of being present at the next template position of the template nucleic acid; (b) monitoring the next template position for ternary complexes formed by the series of mixtures, wherein a signal state indicates presence or absence of ternary complex formed at the next template position by each individual mixture, thereby determining a series of signal states that encodes a base call for the next template position; and (c) decoding the series of signal states to distinguish a correct base call for the next template position from an error in the base call.

In particular embodiments, an encoding scheme is used that identifies valid base calls and distinguishes them from invalid base calls. As such, the encoding scheme provides an error detection code. Useful encoding schemes include those developed for telecommunications, coding theory and information theory such as those set forth in Hamming, *Coding and Information Theory*, $2^{nd}$ Ed. Prentice Hall, Englewood Cliffs, N.J. (1986), which is incorporated herein by reference.

A relatively straightforward error detecting code is a repetition code. In this scheme, a series of examinations are performed at a particular position of a template nucleic acid such that the signal state acquired from each examination is expected to be discrete for each type of ternary complex. For example, the ternary complex formed by each different type of cognate nucleotide can have a unique label and the same label can be used for the respective type of ternary complex in each examination. The signal states detected from the series of examinations can be represented as a series of digits that form a codeword. A base call is identified as valid when the codeword contains only repeated digits, whereas presence of differences between the digits in the codeword indicates an error.

A useful encoding scheme can utilize a parity code. In this scheme, signal states acquired from each examination are represented by a binary digit, for example, '1' for a signal that indicates presence of a ternary complex and '0' for absence of the signal. The signal states detected from a series of examinations can be represented as a series of the digits to form a codeword, the codeword having a length equivalent to the number examinations. Codewords can be assigned such that the total number of '1' digits in the codewords for valid base calls is even or odd. Accordingly, codewords having the selected parity will be identified as valid calls, whereas codewords having the other parity will be identified as invalid calls.

Encoding schemes that use a repetitive code or parity code, although being capable of detecting errors, have limited capabilities when it comes to correcting errors. For example, when using a repetitive code having three or more binary digits, an error can be corrected via majority vote, wherein an aberrant value for one digit is reverted to the same value as the majority of digits in the codeword. This operates much like triple modular redundancy in computing in which three systems perform a process and that result is processed by a majority-voting system to produce a single output. In some embodiments, information from an encoding scheme can be combined with other empirical observations or theoretical expectations to correct an error. For example, the presence of an incorrect value for a digit in a codeword can be correlated with an aberration in a procedure, reagent or apparatus used to produce the digit, and the value of the digit can be changed to compensate for the aberration. Exemplary aberrations that can be corrected include, but are not limited to, a signal to noise ratio below a predetermined threshold, signal intensity below a predetermined threshold, signal intensity above a predetermined threshold, noise above a predetermined threshold, detector malfunction, fluidic delivery malfunction, temperature control malfunction, or reagent quality below a predetermined threshold.

A particularly useful encoding scheme uses a Hamming code. A Hamming code can provide for error detection and, in several embodiments, also provides error correction. In this scheme, signal states detected from a series of examinations can be represented as a series of the digits to form a codeword, the codeword having a length equivalent to the number examinations. The digits can be binary (e.g. having a value of 1 for presence of signal and a value of 0 for absence of the signal) or digits can have a higher radix (e.g. a ternary digit having a value of 1 for luminescence at a first wavelength, a value of 2 for luminescence at a second wavelength and a value of 0 for no luminescence at those wavelengths). Error correction capabilities are provided when invalid codes can be unambiguously changed to a particular valid code due to an appropriate Hamming distance between valid codes. Examples of Hamming codes and their use for error correction are provided in Example 9 below.

An encoding scheme of the present disclosure can use binary digits to represent two signal states. The signal states can be based on any of a variety of distinguishable characteristics for signals obtained for ternary complexes. For example, a binary digit can be assigned values (e.g. represented by symbols such as numbers, letters or the like) for (i) presence and absence of a signal; (ii) signals emitted at two different wavelengths; (iii) signals having two different intensities; or (iv) signals resulting from excitation at two different wavelengths. Alternatively, an encoding scheme can use ternary digits to represent three signal states. Exemplary signal states that can be represented by ternary digits include, but are not limited (i) signals emitted at three different wavelengths; (ii) signals emitted at two different wavelengths and absence of signal at both of those wavelengths; (iii) signals having three different intensities (one of which can be 0 intensity); or (iv) signals resulting from excitation at three different wavelengths.

In particular embodiments, a series of signal states that is obtained from a series of examinations at a particular position of a template can be encoded to include an error correcting code. For example, the series of mixtures that are examined can consist of three mixtures and the series of signal states can be represented by three digits, each digit representing a signal state obtained from a mixture. As set forth previously, each of the signal states can be represented by a binary digit, and the error correcting code can be a repetition code. In this case, an invalid base call can be identified due to an invalid code and the invalid call can be corrected by a majority vote between the three digits.

In a second example of an error correcting code, the series of mixtures consists of four mixtures and the series of signal states is represented by four digits, each digit representing a signal state obtained from a mixture. Furthermore, each of the signal states can be represented by a ternary digit. The error correcting code can be a Hamming code and the Hamming distance between valid base calls can be three. The invalid base can be corrected to a valid base call having a code with the closest Hamming distance to the code for the invalid base call.

In a third example of an error correcting code, the series of mixtures consists of five mixtures and the series of signal states is represented by five digits, each digit representing a signal state obtained from a mixture. Each of the signal states is represented by a binary digit, wherein the error correcting code includes a Hamming code and each valid base call differs from other valid base calls by three digits. Again, the invalid base can be corrected to a valid base call having a code with the closest Hamming distance to the code for the invalid base call.

In particular embodiments, the steps of a nucleic acid detection method set forth herein can be repeated to interrogate several different positions in a template nucleic acid. In some cases, a series of sequential positions along the template can be interrogated. Accordingly, this disclosure provides a method for sequencing a nucleic acid that includes the steps of (a) forming a mixture under ternary complex stabilizing conditions, wherein the mixture includes a primed template nucleic acid, a polymerase and nucleotide cognates of first, second and third base types in the template; (b) examining the mixture to determine whether a ternary complex formed; (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) for the primed template nucleic acid that comprises the extended primer.

Also provided by this disclosure is a method for sequencing a nucleic acid that includes the steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) for the primed template nucleic acid that comprises the extended primer.

In a further embodiment, a method of nucleic acid sequencing can include the steps of (a) contacting a primed template nucleic acid with a polymerase and a first mixture of nucleotides under ternary complex stabilizing conditions, wherein the first mixture includes a nucleotide cognate of a first base type and a nucleotide cognate of a second base type; (b) contacting the primed template nucleic acid with a polymerase and a second mixture of nucleotides under ternary complex stabilizing conditions, wherein the second mixture includes a nucleotide cognate of the first base type and a nucleotide cognate of a third base type; (c) examining products of steps (a) and (b) for signals produced by a ternary complex that includes the primed template nucleic acid, a polymerase and a next correct nucleotide, wherein signals acquired for the product of step (a) are ambiguous for the first and second base type, and wherein signals acquired for the product of step (b) are ambiguous for the first and third base type; (d) disambiguating signals acquired in step (c) to identify a base type that binds the next correct nucleotide; (e) adding a next correct nucleotide to the primer of the primed template nucleic acid after step (c), thereby producing an extended primer; and (f) repeating steps (a) through (e) for the primed template nucleic acid that comprises the extended primer.

Further still, a method of nucleic acid sequencing can include the steps of (a) contacting a primed template nucleic acid with a first mixture including a polymerase, a nucleotide cognate of a first base type in the template and a nucleotide cognate of a second base type in the template, wherein the contact occurs in a binding reaction that (i) stabilizes ternary complexes including the primed template nucleic acid, the polymerase and a next correct nucleotide, and (ii) prevents incorporation of the next correct nucleotide into the primer; (b) examining the binding reaction to determine whether a ternary complex formed; (c) subjecting the primed template nucleic acid to a repetition of steps (a) and (b), wherein the first mixture is replaced with a second mixture, the second mixture including a polymerase, a nucleotide cognate of the first base type in the template and a nucleotide cognate of a third base type in the template; (d) identifying the next correct nucleotide for the primed template nucleic acid using the examination of the binding reaction, or the product thereof, wherein (i) the next correct nucleotide is identified as a cognate of the first base type if ternary complex is detected in step (b) and detected in the repetition of step (b), (ii) the next correct nucleotide is identified as a cognate of the second base type if ternary complex is detected in step (b) and undetected in the repetition of step (b), and (iii) the next correct nucleotide is identified as a cognate of the third base type if ternary complex is undetected in step (b) and detected in the repetition of step (b); (e) adding a next correct nucleotide to the primer of the primed template nucleic acid after step (c), thereby producing an extended primer; and (f) repeating steps (a) through (e) for the primed template nucleic acid that comprises the extended primer.

In some embodiments, a method of nucleic acid sequencing can include the steps of (a) contacting a primed template nucleic acid with a series of mixtures for forming ternary complexes, wherein each of the mixtures includes a polymerase and nucleotide cognates for at least two different base types suspected of being present at the next template position of the template nucleic acid; (b) monitoring the next template position for ternary complexes formed by the series of mixtures, wherein a signal state indicates presence or absence of ternary complex formed at the next template position by each individual mixture, thereby determining a series of signal states that encodes a base call for the next template position; (c) decoding the series of signal states to distinguish a correct base call for the next template position from an error in the base call; (d) adding a next correct nucleotide to the primer of the primed template nucleic acid after step (b), thereby producing an extended primer; and (e) repeating steps (a) through (d) for the primed template nucleic acid that comprises the extended primer.

The next correct nucleotide that is added to the primer in a sequencing method can be reversibly terminated, so as to produce an extended, reversibly terminated primer. Adding a reversibly terminated nucleotide to the 3' end of the primer provides a means to prevent more than one nucleotide from being added to the primer during the extension step and further prevents unwanted extension of the primer in a subsequent examination step. Thus, each position in the template can be examined sequentially. Furthermore, a stabilized ternary complex can be formed at each position and examined to detect the next correct nucleotide for the template that is hybridized to the extended, reversibly terminated primer. The method can be repeated in a step-wise fashion by then removing or modifying the reversible terminator moiety from the extended, reversibly terminated primer to produce an extendible primer.

Typically, a reversibly terminated nucleotide that is added to a primer in a method set forth herein does not have an exogenous label. This is because the extended primer need not be detected in a method set forth herein. However, if desired, one or more types of reversibly terminated nucleotides used in a method set forth herein can be detected, for example, via exogenous labels attached to the nucleotides. Exemplary reversible terminator moieties, methods for incorporating them into primers and methods for modifying the primers for further extension (often referred to as 'deblocking') are set forth in U.S. Pat. Nos. 7,544,794; 7,956,171; 8,034,923; 8,071,755; 8,808,989; or 9,399,798. Further examples are set forth in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other techniques for facilitating repetition of steps in a sequencing method set forth herein include, for example, forming a stabilized ternary complex that can be modified to an extension competent form. For example, an extendible primer can be present in a stabilized ternary complex, but extension can be prevented by the composition of the reaction mixture. In this case, extension can be facilitated by contacting the stabilized ternary complex with a ternary complex destabilizing agent to allow incorporation of the nucleotide in the ternary complex, removing a ternary complex stabilizing agent to allow incorporation of the nucleotide in the ternary complex, or removing the nucleotide and/or polymerase from the stabilized ternary complex and introducing another polymerase and/or nucleotide under conditions that facilitate extension of the primer.

A primer extension step can be carried out by contacting a primed template nucleic acid with an extension reaction mixture. In some cases, the fluid that was present in the examination step is removed and replaced with the extension reaction mixture. Alternatively, the extension reaction mixture can be formed by adding one or more reagents to the fluid that was present in the examination step. Optionally, the incorporation reaction mixture includes a different composition of nucleotides than an examination step. For example, an examination step can include one or more nucleotide types that are not present in the incorporation reaction and vice versa. By way of more specific example, an examination step can omit at least one type of nucleotide and a primer extension step can employ at least four types of nucleotides. Optionally, one or more nucleotide types is added to an examination mixture for a primer extension step.

Nucleotides present in an examination step may cause unwanted nucleotide incorporation if carried over into an extension step. Thus, a wash step can be employed prior to a primer extension step to remove nucleotides. Optionally, free nucleotides may be removed by enzymes such as phosphatases, by chemical modification or by physical separation techniques.

Optionally, a nucleotide enclosed within a stabilized ternary complex of an examination step is incorporated into the 3'-end of a primer during a subsequent primer extension step. Alternatively, a primer extension step includes replacing a nucleotide from a prior examination step and incorporating another nucleotide (of the same or different type) into the 3'-end of the primer.

Optionally, a polymerase present during an examination step is removed and replaced with a different polymerase for a subsequent primer extension step. Alternatively, the polymerase present during the examination step is retained and modified for a subsequent incorporation step. Optionally, one or more nucleotides present during an examination step are modified for a subsequent primer extension step. A fluid, reagent or condition that is present during an examination step may be altered by any of a variety of techniques for use in a subsequent primer extension step. Exemplary techniques include, but are not limited to, removing reagents, chelating reagents, diluting reagents, adding reagents, altering reaction conditions such as temperature, ionic strength, conductivity or pH, or any combination thereof. The reagents in a reaction mixture including any combination of polymerase, primed template nucleic acid, and nucleotide may be modified during an examination step and/or primer extension step.

Typically, an extension step employed in a method set forth herein will result in addition of a nucleotide cognate for any base type that is expected to be present in a template nucleic acid. For example, primer extension can be carried out under conditions that result in incorporation of cognate nucleotides for all four base types that are present in DNA (e.g. adenine, thymine, guanine and cytosine) or RNA (e.g. adenine, uracil, guanine and cytosine). The different nucleotide types can be present simultaneously in an extension reaction, or they can participate in serial extension reactions. For example, some or all of the nucleotide types can been delivered simultaneously in a single extension reaction. Alternatively, different nucleotide types can be serially delivered (individually or in subsets) such that they are combined into a single extension reaction or such that serial extension reactions occur.

Although extension has been exemplified above with regard to the use of cognates for four base types in a template, it will be understood that a larger repertoire of nucleotides can be used. The number of nucleotide types can increase, for example, when using templates having one or both members of an unnatural base pair. In some embodiments, it may be desirable to extend a primer with cognates for only a subset of base types that are expected to be present in a template. Thus, it is possible to include cognates for fewer than 6, 5, 4, 3 or 2 base types. Alternatively or additionally, a method set forth herein can be used to extend a primer with cognates for at least 1, 2, 3, 4, 5, 6 or more base types.

A sequencing method can include multiple repetitions of steps set forth herein. For example, examination and extension steps can be repeated multiple times as can optional steps of deblocking primers, or washing away unwanted reactants or products between various steps. Accordingly, a primed template nucleic acid can be subjected at least 2, 5, 10, 25, 50, 100 or more steps of a method set forth herein. Not all of the steps need to be repeated nor do repeated steps need to occur in the same order in each repetition. For example, next correct nucleotides at each position of a template can be identified using real time analysis (i.e. in parallel with fluidic and detection steps of a sequencing method). However, real time analysis is not necessary and instead next correct nucleotides can be identified after some or all of the fluidic and detection steps have been completed. Accordingly, signals from at least some Sequencing By Binding™ cycles can be disambiguated and/or the identity of nucleotide types for at least some cycles can be imputed while fluidic steps are occurring. Optionally, signals can be disambiguated and/or the identity of non-detected nucleotide types can be imputed after some or all of the fluidic and detection cycles have been completed.

A primer extension step need not use a labeled polymerase. For example, a polymerase that is used for an extension step need not be attached to an exogenous label (e.g. covalently or otherwise). However, a polymerase that is used for primer extension can include an exogenous label, for example, a label that was used in a previous examination step.

As set forth above, different activities of polymerases can be exploited in a method set forth herein. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and $\kappa$, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and Kl1 polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most genotyping and sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Examples of reagents and conditions that can be used for a polymerase-based primer extension step include, for example, those set forth in commonly owned U.S. Pat. App. Pub. No. 2017/0022553 A1 or U.S. Pat. App. Pub. No. 2018/0044727 A1, which claims priority to U.S. patent application Ser. No. 62/447,319; or U.S. patent application Ser. No. 15/851,383, which claims benefit of U.S. patent application Ser. No. 62/440,624; or U.S. patent application Ser. No. 15/873,343, which claims priority to U.S. patent application Ser. No. 62/450,397, each of which is incorporated herein by reference. Other useful reagent and conditions for polymerase-based primer extension are set forth in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Optionally, the provided methods further include one or more wash steps. A wash step can occur before or after any other step in the method. For example, a method set forth herein can optionally include a step of washing a solid support after forming one or more stabilized ternary complexes. The wash can provide the advantage of removing contaminants such as components of a mixture from which one or more components of the stabilized ternary complex were derived. In particular embodiments, the wash step occurs under conditions that stabilize the ternary complex. For example, one or more of the stabilizing conditions or stabilizing agents set forth elsewhere herein can be employed during a wash step. Optionally, the wash solution includes nucleotide(s) of the same type as the next correct nucleotide(s) used during formation of the stabilized ternary complex. Including the next correct nucleotide(s) at a sufficient concentration can provide the advantage of stabilizing previously formed ternary complexes from unwanted disassociation. This in turn prevents unwanted reduction in detection sensitivity due to washing away previously formed ternary complexes. Optionally, the ternary complex has a half-life and the wash step is performed for a duration shorter than the half-life of the ternary complex. Wash steps can also be carried out after examination or primer extension steps.

A stabilized ternary complex, or a component that is capable of forming (i.e. participating in the formation of) a ternary complex, can be attached to a solid support. The solid support can be made from any of a variety of materials set forth herein. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A particularly useful solid support is a particle such as a bead or microsphere. Populations of beads can be used for attachment of populations of stabilized ternary complexes or components capable of forming the complexes (e.g. polymerases, templates, primers or nucleotides). In some embodiments, it may be useful to use a configuration whereby each bead has a single type of stabilized ternary complex or a single type of component capable of forming the complex. For example, an individual bead can be attached to a single type of ternary complex, a single type of template allele, a single type of allele-specific primer, a single type of locus-specific primer or a single type of nucleotide. Alternatively, different types of components need not be separated on a bead-by-bead basis. As such, a single bead can bear multiple different types of ternary complexes, template nucleic acids, primers, primed template nucleic acids and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methyl styrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere can correspond to a wide variety of different forms and shapes. For example, they can be symmetrically shaped (e.g. spherical or cylindrical) or irregularly shaped (e.g. controlled pore glass). In addition, beads can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel in a method set forth herein. Although it is also possible to serially process different types of nucleic acids using one or more steps of the methods set forth herein, parallel processing can provide cost savings, time savings and uniformity of conditions. An apparatus or method of the present disclosure can include at least 2, 10, 100, $1\times10^3$, $1\times10^4$, $1\times10^5$, $1\times10^6$, $1\times10^9$, or more different nucleic acids. Alternatively or additionally, an apparatus or method of the present disclosure can include at most $1\times10^9$, $1\times10^6$, $1\times10^5$, $1\times10^4$, $1\times10^3$, 100, 10, 2 or fewer, different nucleic acids. Accordingly, various reagents or products set forth herein as being useful in the apparatus or methods (e.g. primed template nucleic acids or stabilized ternary complexes) can be multiplexed to have different types or species in these ranges.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a support in a way that provides detection at a single molecule level or at an ensemble level. For example, a plurality of different nucleic acids can be attached to a solid support in a way that an individual stabilized ternary complex that forms on one nucleic acid molecule on the support can be distinguished from all neighboring ternary complexes that form on the nucleic acid molecules of the support. As such, one or more different templates can be attached to a solid support in a format where each single molecule template is physically isolated and detected in a way that the single molecule is resolved from all other molecules on the solid support.

Alternatively, a method of the present disclosure can be carried out for one or more nucleic acid ensembles, an ensemble being a population of nucleic acids having a common template sequence. Cluster methods can be used to attach one or more ensembles to a solid support. As such, an array can have a plurality of ensembles, each of the ensembles being referred to as a cluster or array feature in that format. Clusters can be formed using methods known in the art such as bridge amplification or emulsion PCR. Useful bridge amplification methods are described, for example, in U.S. Pat. Nos. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., Proc. Natl. Acad. Sci. USA 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface is rolling circle amplification (RCA), for example, as described in Lizardi et al., Nat. Genet. 19:225-232 (1998) or US 2007/0099208 A1, each of which is incorporated herein by reference.

In particular embodiments, a stabilized ternary complex, polymerase, nucleic acid or nucleotide is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

One or more images can be obtained from an array. For example a series of images can be obtained for a series of examinations carried out during a particular sequencing cycle. Each images can undergo image registration to determine the location of features, signal intensities can be extracted from the images, and signal intensities can be normalized, if desired. In each image, the intensities can be separated into on and off intensities using a binary segmentation method, such as Otsu's method. In some embodiments multiple emission colors are detected and a different image is acquired for each color. The emission intensities from each image can be analyzed using a clustering algorithm such as k means or a Gaussian mixture model to determine which of several states (e.g. blue emission, red emission, or dark) a feature belongs. For each feature these signal processing techniques will yield a series of signal states from the series images. Each feature can be represented as a codeword consisting of a series of digits representing the signal states from the series of images. If the codeword matches one of the four allowed codewords for a valid base, then the appropriate base call is made. Otherwise a null base call can be made. However, if an error correcting code is used then an invalid codeword for a particular feature can be changed to a valid codeword to correct the base call.

Nucleic acids that are used in a method or composition herein can be DNA such as genomic DNA, synthetic DNA, amplified DNA, copy DNA (cDNA) or the like. RNA can also be used such as mRNA, ribosomal RNA, tRNA or the like. Nucleic acid analogs can also be used as templates herein. Thus, template nucleic acids used herein can be derived from a biological source, synthetic source or amplification product. Primers used herein can be DNA, RNA or analogs thereof.

Particularly useful nucleic acid templates are genome fragments that include sequences identical to a portion of a genome. A population of genome fragments can include at least 5%, 10%, 20%, 30%, or 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more nucleotides of a genome. A genome fragment can be DNA, RNA, or an analog thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii*, *Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli*, staphylococci or *mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

The present disclosure provides systems for detecting nucleic acids, for example, using methods set forth herein. For example, a system can be configured for genotyping reactions or Sequencing By Binding™ reactions involving the examination of the interaction between a polymerase and a primed template nucleic acid in the presence of nucleotides to identify the next base in the template nucleic acid sequence. Optionally, a system includes components and reagents for performing one or more steps set forth herein including, but not limited to, forming at least one stabilized ternary complex between a primed template nucleic acid, polymerase and next correct nucleotide, detecting the stabilized ternary complex(es), extending the primer of each primed template with a next correct nucleotide, and/or identifying a nucleotide or sequence of nucleotides present in the template.

A system of the present disclosure can include a vessel or solid support for carrying out a nucleic acid detection method. For example, the system can include an array, flow cell, multi-well plate or other convenient apparatus. The vessel or solid support can be removable, thereby allowing it to be placed into or removed from the system. As such, a system can be configured to sequentially process a plurality of vessels or solid supports. The system can include a fluidic system having reservoirs for containing one or more of the reagents set forth herein (e.g. polymerase, primer, template nucleic acid, nucleotide(s) for ternary complex formation, nucleotides for primer extension, deblocking reagents or mixtures of such components). The fluidic system can be configured to deliver reagents to a vessel or solid support, for example, via channels or droplet transfer apparatus (e.g. electrowetting apparatus). Any of a variety of detection apparatus can be configured to detect the vessel or solid support where reagents interact. Examples include luminescence detectors, surface plasmon resonance detectors and others known in the art. Exemplary systems having fluidic and detection components that can be readily modified for use in a system herein include, but are not limited to, those set forth in US patent application Ser. Nos. 62/481,289 or 62/545,606; U.S. Pat. Nos. 8,241,573; 7,329,860 or 8,039,817; or US Pat. App. Pub. Nos. 2009/0272914 A1 or 2012/0270305 A1, each of which is incorporated herein by reference.

Optionally, a system of the present disclosure further includes a computer processing unit (CPU) that is configured to operate system components. The same or different CPU can interact with the system to acquire, store and process signals (e.g. signals detected in a method set forth herein). In particular embodiments, a CPU can be used to determine, from the signals, the identify the nucleotide that is present at a particular location in a template nucleic acid. In some cases, the CPU will identify a sequence of nucleotides for the template from the signals that are detected. In particular embodiments, the CPU is programmed to compare signals obtained from different binding reactions to disambiguate signals, thereby identifying nucleotides at one or more position in a template nucleic acid. Alternatively or additionally, a CPU can be programmed to compare signals obtained from different binding reactions to identify a nucleotide at one or more position in a template nucleic acid by imputation. Accordingly, a CPU can be programmed to decode an error detecting code, to decode an error correcting code, or to correct an error in a codeword obtained from a method set forth herein.

A useful CPU can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks such as processing of signals detected in a method set forth herein, disambiguating signals to identify nucleotides or imputing nucleotide identity where signals for other types of nucleotides are detected.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a use with the nucleic acid detection system. Similarly, the CPU can communicate with other devices (e.g., via network card, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

This disclosure further provides a kit for distinguishing nucleotides in a nucleic acid template. The kit can include reagents for carrying out one or more of the methods set forth herein. For example, a kit can include reagents for producing a stabilized ternary complex when mixed with one or more primed template nucleic acid. More specifically, a kit can include one or more of the mixtures of nucleotides used in a method set forth herein, including for example, the methods set forth in the Examples section below. In addition to the nucleotide mixtures the kit can include a polymerase that is capable of forming a stabilized ternary complex. The nucleotides, polymerase or both can include an exogenous label, for example, as set forth herein in the context of various methods.

In some embodiments, the kit can be configured to support a repetitive method such as a Sequencing By Binding™ method. Accordingly, a kit can further include reagents for carrying out primer extension. Exemplary reagents for primer extension can include a polymerase and mixture of four nucleotide types. The nucleotide types used for extension can optionally include reversible terminating groups. In this option, the kit can further include reagents for deblocking a primer that has incorporated the reversibly terminated nucleotides.

Accordingly, any of the components or articles used in performing the methods set forth herein can be usefully packaged into a kit. For example, the kits can be packed to include some, many or all of the components or articles used in performing the methods set forth herein. Exemplary components include, for example, nucleotides, polymerases, terminator moieties, deblocking reagents and the like as set forth herein and in references cited herein. Any of such reagents can include, for example, some, many or all of the buffers, components and/or articles used for performing one or more of the subsequent steps for analysis of a primed template nucleic acid. A kit need not include a primer or template nucleic acid. Rather, a user of the kit can provide a primed template nucleic acid which is to be combined with components of the kit.

One or more ancillary reagents also can be included in a kit. Such ancillary reagents can include any of the reagents exemplified above and/or other types of reagents useful in performing the methods set forth herein. Instructions can further be included in a kit. The instructions can include, for example, procedures for making any components or articles used in the methods set forth herein, performing one or more steps of any embodiment of the methods set forth herein and/or instructions for performing any of the subsequent analysis steps employing a primed template nucleic acid.

In particular embodiments, a kit includes a cartridge having reservoirs to contain the reagents and further having fluidic components for transferring reagents from the reservoirs to a detection instrument. For example, the fluidic components can be configured to transfer reagents to a flow cell where stabilized ternary complexes are detected. An exemplary fluidic cartridge that can be included in a kit (or system) of the present disclosure is described in U.S. patent application Ser. No. 62/481,289, which is incorporated herein by reference.

NUMBERED EMBODIMENTS

Embodiment 1. A method of nucleic acid detection, comprising steps of:

(a) contacting a primed template nucleic acid with a polymerase and a first mixture of nucleotides under conditions for stabilizing a ternary complex at a nucleotide position in the template, wherein the first mixture comprises a nucleotide cognate of a first base type and a nucleotide cognate of a second base type;

(b) contacting the primed template nucleic acid with a polymerase and a second mixture of nucleotides under conditions for stabilizing a ternary complex at the nucleotide position in the template, wherein the second mixture comprises a nucleotide cognate of the first base type and a nucleotide cognate of a third base type;

(c) examining products of steps (a) and (b) for signals produced by a ternary complex that comprises the primed template nucleic acid, a polymerase and a next correct nucleotide, wherein signals acquired for the product of step (a) are ambiguous for the first and second base type, and wherein signals acquired for the product of step (b) are ambiguous for the first and third base type;

(d) disambiguating signals acquired in step (c) to identify a base type that binds the next correct nucleotide.

Embodiment 2. The method of embodiment 1, wherein the primed template nucleic acid is not in contact with a nucleotide cognate of a fourth base type during step (c).

Embodiment 3. The method of embodiment 2, wherein (i) the first base type is correlated with presence of signals for the product of step (a) and presence of signals for the product of step (b), (ii) the second base type is correlated with presence of signals for the product of step (a) and absence of signals for the product of step (b), and (iii) the third base type is correlated with absence of signals for the product of step (a) and presence of signals for the product of step (b).

Embodiment 4. The method of embodiment 3, wherein the first mixture lacks nucleotide cognates of the third and fourth base types, and wherein the second mixture lacks nucleotide cognates of the second and fourth base types.

Embodiment 5. The method of embodiment 4, wherein (iv) the fourth base type is correlated with absence of signals for the product of step (a) and absence of signals for the product of step (b).

Embodiment 6. The method of embodiment 1, wherein the first mixture further comprises nucleotide cognates of the third and fourth base types, wherein the product of step (a) produces a first signal for stabilized ternary complex that comprises the nucleotide cognate of the first base type and for stabilized ternary complex that comprises the nucleotide cognate of the second base type, wherein the product of step (a) produces a second signal for stabilized ternary complex that comprises the nucleotide cognate of the third base type and for stabilized ternary complex that comprises the nucleotide cognate of the fourth base type, and wherein the examining of the products of step (a) distinguishes the first signal from the second signal.

Embodiment 7. The method of embodiment 6, wherein the second mixture further comprises nucleotide cognates of the second and fourth base types, wherein the product of step (b) produces the first signal for stabilized ternary complex that comprises the nucleotide cognate of the first base type and for stabilized ternary complex that comprises the nucleotide cognate of the third base type, and wherein the product of step (b) produces the second signal for stabilized ternary complex that comprises the nucleotide cognate of the second base type and for stabilized ternary complex that comprises the nucleotide cognate of the fourth base type.

Embodiment 8. The method of embodiment 7, wherein (i) the first base type is correlated with presence of the first signal for the products of steps (a) and (b), (ii) the second base type is correlated with presence of the first signal for the product of step (a) and presence of the second signal for the product of step (b), (iii) the third base type is correlated with presence of the second signal for the product of step (a) and presence of the first signal for the product of step (b), and (iv) the fourth base type is correlated with presence of the second signal for the product of steps (a) and (b).

Embodiment 9. The method of embodiment 6, wherein the second mixture further comprises nucleotide cognates of the second and fourth base types, wherein the product of step (b) produces the first signal for stabilized ternary complex that comprises the nucleotide cognate of the first base type and for stabilized ternary complex that comprises the nucleotide cognate of the third base type, and wherein the product of step (b) produces the no signal for stabilized ternary complex that comprises the nucleotide cognate of the second base type and for stabilized ternary complex that comprises the nucleotide cognate of the fourth base type.

Embodiment 10. The method of embodiment 9, wherein (i) the first base type is correlated with presence of the first signal for the products of steps (a) and (b), (ii) the second base type is correlated with presence of the first signal for the product of step (a) and absence of signal for the product of step (b), (iii) the third base type is correlated with presence of the second signal for the product of step (a) and presence of the first signal for the product of step (b), and (iv) the fourth base type is correlated with presence of the second signal for the product of step (a) and absence of signal for the product of step (b).

Embodiment 11. The method of any one of embodiments 1 to 10, wherein the signals acquired in step (c) are produced by exogenous labels attached to polymerases.

Embodiment 12. The method of embodiment 1 or 11, wherein the signals for the products of step (a) are acquired by a detector that is also used to detect the signals for the products of step (b).

Embodiment 13. The method of any one of embodiments 1 to 12, wherein the signals for the products of steps (a) and (b) comprise luminescent signals.

Embodiment 14. The method of any one of embodiments 1 to 13, wherein the nucleotides in the first mixture do not comprise exogenous labels.

Embodiment 15. The method of embodiment 14, wherein the nucleotides in the second mixture do not comprise exogenous labels.

Embodiment 16. The method of any one of embodiments 1 to 13, wherein the first mixture does not comprise labels that distinguish the nucleotide cognate of the first base type from the nucleotide cognate of the second base type.

Embodiment 17. The method of embodiment 16, wherein the second mixture does not comprise labels that distinguish the nucleotide cognate of the first base type from the nucleotide cognate of the third base type.

Embodiment 18. The method of any one of embodiments 1 to 17, further comprising (e) adding a reversibly terminated, next correct nucleotide to the primer of the primed template nucleic acid after step (c), thereby producing an extended, reversibly terminated primer.

Embodiment 19. The method of embodiment 18, further comprising repeating steps (a) through (c) for the primed template nucleic acid that comprises the extended, reversibly terminated primer.

Embodiment 20. The method of embodiment 19, further comprising (f) removing the reversible terminator moiety from the extended, reversibly terminated primer after steps (a) through (c) are repeated.

Embodiment 21. The method of embodiment 19, wherein step (e) is carried out prior to step (d).

Embodiment 22. The method of any one of embodiments 1 to 21, wherein the polymerase of step (a) is replaced with the polymerase of step (b).

Embodiment 23. The method of any one of embodiments 1 to 22, wherein the same type of polymerase is present in steps (a) and (b).

Embodiment 24. The method of embodiment 1, comprising a further step of contacting the primed template nucleic acid with a polymerase and a nucleotide cognate of a fourth base type, wherein step (c) further comprises examining products of the further step for signals produced by a ternary complex that comprises the primed template nucleic acid, a polymerase and a next correct nucleotide.

Embodiment 25. The method of embodiment 24, wherein (iv) the fourth base type is correlated with presence of signals for the product of the further step.

Embodiment 26. The method of any one of embodiments 1 to 25, wherein the steps are carried out for a plurality of primed template nucleic acids having different sequences.

Embodiment 27. The method of embodiment 26, wherein the plurality of primed template nucleic acids is attached to an array.

Embodiment 28. The method of any one of embodiments 1 to 27, further comprising removing the first mixture from the primed template nucleic acid prior to step (b).

Embodiment 29. The method of any one of embodiments 1 to 28, wherein the examining of the products of step (a) is carried out prior to step (b).

Embodiment 30. The method of embodiment 1, further comprising
(i) contacting the primed template nucleic acid with a polymerase and a third mixture of nucleotides under conditions for stabilizing a ternary complex at the nucleotide position in the template, wherein the third mixture comprises a nucleotide cognate of the second base type and a nucleotide cognate of a fourth base type;
(ii) contacting the primed template nucleic acid with a polymerase and a fourth mixture of nucleotides under conditions for stabilizing a ternary complex at the nucleotide position in the template, wherein the fourth mixture comprises a nucleotide cognate of the third base type and a nucleotide cognate of the fourth base type; and
(iii) examining products of steps (i) and (ii) for signals produced by a ternary complex that comprises the primed template nucleic acid, a polymerase and a next correct nucleotide, wherein signals acquired for the product of step (i) are ambiguous for the second and fourth base type, and wherein signals acquired for the product of step (ii) are ambiguous for the third and fourth base type.

Embodiment 31. The method of embodiment 30, wherein the first mixture lacks nucleotide cognates of the third or fourth base types.

Embodiment 32. The method of embodiment 31, wherein the second mixture lacks nucleotide cognates of the second or fourth base types, wherein the third mixture lacks nucleotide cognates of the first or third base types, and wherein the fourth mixture lacks nucleotide cognates of the first or second base types.

Embodiment 33. The method of embodiment 30, wherein the first mixture comprises a labeled nucleotide cognate of the first base type and a labeled nucleotide cognate of the second base type, and wherein the first mixture comprises a non-labeled nucleotide cognate of the third or fourth base types.

Embodiment 34. The method of embodiment 33, wherein the second mixture comprises a labeled nucleotide cognate of the first base type and a labeled nucleotide cognate of the third base type, wherein the second mixture comprises a non-labeled nucleotide cognate of the second or fourth base types, Embodiment 35. The method of embodiment 34, wherein the third mixture comprises a labeled nucleotide cognate of the second base type and a labeled nucleotide cognate of the fourth base type, wherein the third mixture comprises a non-labeled nucleotide cognate of the first or third base types.

Embodiment 36. The method of embodiment 35, wherein the fourth mixture comprises a labeled nucleotide cognate of the third base type and a labeled nucleotide cognate of the fourth base type, wherein the fourth mixture comprises a non-labeled nucleotide cognate of the first or second base types.

Embodiment 37. A method of nucleic acid detection, comprising:
(a) forming a mixture under ternary complex stabilizing conditions, wherein the mixture comprises a primed template nucleic acid, a polymerase and nucleotide cognates of first, second and third base types in the template;
(b) examining the mixture to determine whether a ternary complex formed; and
(c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

Embodiment 38. The method of embodiment 37, wherein the primed template nucleic acid is not in contact with a nucleotide cognate of the fourth base type during step (b).

Embodiment 39. The method of embodiment 37 or 38, wherein the polymerase is attached to an exogenous label.

Embodiment 40. The method of embodiment 39, wherein the nucleotide cognates do not comprise exogenous labels.

Embodiment 41. The method of embodiment 37 or 38, wherein the nucleotide cognates comprise exogenous labels that distinguish the cognates of first, second and third base types from each other.

Embodiment 42. The method of any one of embodiments 37 to 41, further comprising (d) adding a reversibly terminated, next correct nucleotide to the primer of the primed template nucleic acid after step (b), thereby producing an extended, reversibly terminated primer.

Embodiment 43. The method of embodiment 42, further comprising repeating steps (a) and (b) for the primed template nucleic acid that comprises the extended, reversibly terminated primer.

Embodiment 44. The method of embodiment 43, further comprising (e) removing the reversible terminator moiety from the extended, reversibly terminated primer after steps (a) and (b) are repeated.

Embodiment 45. The method of embodiment 42, wherein step (d) is carried out prior to step (c).

Embodiment 46. The method of any one of embodiments 37 to 45, wherein the steps are carried out for a plurality of primed template nucleic acids having different sequences.

Embodiment 47. The method of embodiment 46, wherein the plurality of primed template nucleic acids is attached to an array.

Embodiment 48. A method of nucleic acid detection, comprising:
(a) sequentially contacting a primed template nucleic acid with at least two separate mixtures under ternary complex stabilizing conditions, wherein the at least two separate mixtures each comprise a polymerase and a nucleotide, whereby the sequentially contacting results in the primed template nucleic acid being contacted, under the ternary complex stabilizing conditions, with nucleotide cognates for first, second and third base types in the template;
(b) examining the at least two separate mixtures to determine whether a ternary complex formed; and
(c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

Embodiment 49. The method of embodiment 48, wherein the primed template nucleic acid is not in contact with a nucleotide cognate of the fourth base type during step (b).

Embodiment 50. The method of embodiment 48 or 49, wherein the polymerase is attached to an exogenous label.

Embodiment 51. The method of embodiment 50, wherein the nucleotide cognates do not comprise exogenous labels.

Embodiment 52. The method of any one of embodiment 48 to 50, wherein the nucleotide cognates comprise exogenous labels that distinguish the cognates of first, second and third base types from each other.

Embodiment 53. The method of any one of embodiments 48 to 52, further comprising (d) adding a reversibly terminated, next correct nucleotide to the primer of the primed template nucleic acid after step (b), thereby producing an extended, reversibly terminated primer.

Embodiment 54. The method of embodiment 53, further comprising repeating steps (a) and (b) for the primed template nucleic acid that comprises the extended, reversibly terminated primer.

Embodiment 55. The method of embodiment 54, further comprising (e) removing the reversible terminator moiety from the extended, reversibly terminated primer after steps (a) and (b) are repeated.

Embodiment 56. The method of embodiment 53, wherein step (d) is carried out prior to step (c).

Embodiment 57. The method of any one of embodiments 48 to 56, wherein the steps are carried out for a plurality of primed template nucleic acids having different sequences.

Embodiment 58. The method of embodiment 57, wherein the plurality of primed template nucleic acids is attached to an array.

Embodiment 59. The method of embodiment 48, wherein the sequentially contacting of the primed template nucleic acid with the at least two separate mixtures comprises:
(i) contacting the primed template nucleic acid with a polymerase and a first mixture of nucleotides under ternary complex stabilizing conditions, wherein the first mixture comprises a nucleotide cognate of a first base type and a nucleotide cognate of a second base type, and
(ii) contacting the primed template nucleic acid with a polymerase and a second mixture of nucleotides under ternary complex stabilizing conditions, wherein the second mixture comprises a nucleotide cognate of the first base type and a nucleotide cognate of a third base type.

Embodiment 60. The method of embodiment 59, wherein step (b) comprises detecting signals from the ternary complexes, wherein the signals do not distinguish ternary complexes comprising the nucleotide cognate of the first base type from ternary complexes comprising the nucleotide cognate of the second base type.

Embodiment 61. The method of embodiment 60, wherein the signals do not distinguish ternary complexes comprising the nucleotide cognate of the first base type from ternary complexes comprising the nucleotide cognate of the third base type.

Embodiment 62. The method of embodiment 59, wherein the nucleotides in the first mixture do not comprise exogenous labels.

Embodiment 63. The method of embodiment 62, wherein the nucleotides in the second mixture do not comprise exogenous labels.

Embodiment 64. The method of embodiment 59, wherein the first mixture does not comprise labels that distinguish the nucleotide cognate of the first base type from the nucleotide cognate of the second base type.

Embodiment 65. The method of embodiment 64, wherein the second mixture does not comprise labels that distinguish the nucleotide cognate of the first base type from the nucleotide cognate of the third base type.

Embodiment 66. The method of embodiment 59, wherein the examination comprises detecting signals from a label attached to the nucleotide cognate of the first base type that are the same as signals detected for a label attached to the nucleotide cognate of the second base type.

Embodiment 67. The method of embodiment 66, wherein the examination comprises detecting signals from a label attached to the nucleotide cognate of the first base type that are the same as signals detected for a label attached to the nucleotide cognate of the third base type.

Embodiment 68. The method of embodiment 59, wherein the same type of polymerase is used in (i) and in (ii).

Embodiment 69. The method of embodiment 59, wherein the type of polymerase in (i) is different from the type of polymerase in (ii).

Embodiment 70. The method of embodiment 59, wherein the signals for the products of (i) are acquired by a detector that is also used to detect the signals for the products of (ii).

Embodiment 71. A method of nucleic acid detection, comprising:
(a) sequentially contacting a primed template nucleic acid with first and second mixtures under ternary complex stabilizing conditions, wherein each of the mixtures comprises a polymerase and nucleotide cognates for at least two of four different base types in the primed template nucleic acid, wherein the mixtures differ by at least one type of nucleotide cognate;

(b) examining the first and second mixtures, or products thereof, separately to detect ternary complexes; and (c) identifying the next correct nucleotide for the primed template nucleic acid molecule, wherein the next correct nucleotide is identified as a cognate of one of the four different base types if ternary complex is detected in the two mixtures.

Embodiment 72. The method of embodiment 71, wherein the first mixture comprises a nucleotide cognate of a first base type and a nucleotide cognate of a second base type, and wherein the second mixture comprises a nucleotide cognate of the first base type and a nucleotide cognate of a third base type.

Embodiment 73. The method of embodiment 72, wherein a third mixture is contacted with the primed template nucleic acid, the third mixture comprising a nucleotide cognate of the second base type and a nucleotide cognate of a fourth base type.

Embodiment 74. The method of embodiment 72, wherein a fourth mixture is contacted with the primed template nucleic acid, the fourth mixture comprising a nucleotide cognate of the third base type and a nucleotide cognate of the fourth base type.

Embodiment 75. The method of embodiment 74, wherein the first mixture lacks nucleotide cognates of the third and fourth base types, wherein the second mixture lacks nucleotide cognates of the second and fourth base types, wherein the third mixture lacks nucleotide cognates of the first and third base types, and wherein the fourth mixture lacks nucleotide cognates of the first and second base types.

Embodiment 76. The method of embodiment 71, wherein the first mixture comprises a labeled nucleotide cognate of a first base type and a labeled nucleotide cognate of a second base type, and wherein the first mixture comprises a non-labeled nucleotide cognate of a third or fourth base types.

Embodiment 77. The method of embodiment 76, wherein the second mixture comprises a labeled nucleotide cognate of the first base type and a labeled nucleotide cognate of the third base type, wherein the second mixture comprises a non-labeled nucleotide cognate of the second or fourth base types.

Embodiment 78. The method of embodiment 77, wherein a third mixture is contacted with the primed template nucleic acid, the third mixture comprising a labeled nucleotide cognate of the second base type and a labeled nucleotide cognate of the fourth base type, wherein the third mixture comprises a non-labeled nucleotide cognate of the first or third base types.

Embodiment 79. The method of embodiment 78, wherein a fourth mixture is contacted with the primed template nucleic acid, the fourth mixture comprising a labeled nucleotide cognate of the third base type and a labeled nucleotide cognate of the fourth base type, wherein the fourth mixture comprises a non-labeled nucleotide cognate of the first or second base types.

Embodiment 80. The method of embodiment 71, wherein step (a) comprises sequentially contacting the primed template nucleic acid with at least four mixtures under ternary complex stabilizing conditions, wherein each of the mixtures comprises a polymerase and nucleotide cognates for at least two of four different base types in the primed template nucleic acid, wherein the mixtures differ by at least one type of nucleotide cognate.

Embodiment 81. The method of embodiment 80, wherein the next correct nucleotide is identified as a cognate of one of the four different base types if ternary complex is detected in at least two of the mixtures.

Embodiment 82. The method of embodiment 81, wherein each of the mixtures comprises nucleotide cognates for at least two and no more than three of the four different base types in the primed template nucleic acid.

Embodiment 83. The method of embodiment 81, wherein each of the mixtures comprises nucleotide cognates for at least two and no more than two of the four different base types in the primed template nucleic acid.

Embodiment 84. The method of embodiment 81, wherein each of the mixtures comprises nucleotide cognates for at least three and no more than three of the four different base types in the primed template nucleic acid.

EXAMPLES

The following Examples describe several different configurations that utilize disambiguation and/or imputation to identify nucleotides at individual positions of nucleic acids. Several embodiments utilize an encoding scheme that provides detection of base call errors or correction of invalid base calls.

A primed template nucleic acid is attached to a solid support in a flow cell. Reagents are delivered to the flow cell under conditions for stabilizing formation of a ternary complex between the primed template, polymerase and next correct nucleotide. The tables below refer to a reagent delivery as a 'flow.' The number of reagent flows and composition of each reagent flow can vary as specified for each configuration below. Furthermore, the reagents listed for each flow can be delivered simultaneously or sequentially.

A stabilized ternary complex that forms on the solid support can include a fluorescent label on either the polymerase or nucleotide, as specified in the individual configurations below. Examinations are carried out to detect fluorescent signals on the solid support. The flow cell can optionally be washed between each flow and examination to remove background label and allow better signal to noise in detecting stabilized ternary complex formed on the solid support. Ternary complexes are stabilized and examined using techniques and apparatus set forth in U.S. Pat. App. Pub. No. 2017/0022553 A1 or U.S. patent application Ser. Nos. 62/447,319; 62/440,624 or 62/450,397, each of which is incorporated herein by reference.

Exemplary advantages for each configuration are set forth below. It will be understood that reducing the number of detection channels generally allows use of more affordable detection apparatus, faster image acquisition time and in some cases higher resolution. Reducing the number of flows can provide for faster overall cycle time (i.e. the cumulative fluidic and detection time to interrogate each position in the current example), lower overall cost of reagents and reduced volume of fluidic waste. Reducing the number of different nucleotides can provide lower cost for completing a cycle, reduced overall volume of reagents during shipment and storage, and reduced volume of fluidic waste.

Example 1

One Color, Three Nucleotide Types, Three Deliveries

As shown in the first column of Table 1, three flows can be carried out, each to deliver a polymerase and one nucleotide type to the primed template. In each case either the polymerase or the nucleotide can be attached to a fluorescent label. Examinations are carried out after each flow. The fluorescent label can be the same for all flows. The signal expected for a stabilized ternary complex formed with respective nucleotide types, A, G, C and T, are indicated in the last four columns. A positive sign indicates that a fluorescent signal is detected and a negative sign indicates absence of significant signal. As is evident from Table 1, the presence of a ternary complex where the next correct nucleotide is A, G or C can be determined from a signal detected following the flow where the respective nucleotide was delivered. The nucleotide that was not delivered (i.e. the T nucleotide in this example) is imputed from the absence of significant signal detected in all three examination steps. Note that absence of signal for T or any other nucleotide may be due to absence of the nucleotide in the flow. Alternatively, the non-detected nucleotide may be present in the flow and capable of forming ternary complexes, albeit ternary complexes that are not detectable (e.g. due to absence of a label on the ternary complex formed with that nucleotide).

TABLE 1

| Step | A | G | C | T |
|---|---|---|---|---|
| Flow pol + A | | | | |
| $1^{st}$ Exam | (+) | (−) | (−) | (−) |
| Flow pol + G | | | | |
| $2^{nd}$ Exam | (−) | (+) | (−) | (−) |
| Flow pol + C | | | | |
| $3^{rd}$ Exam | (−) | (−) | (+) | (−) |

An advantage of the configuration in Table 1 is that four nucleotides can be distinguished using only one label, a single detection channel (i.e. excitation and emission collection at the same wavelength for the products of all flows), only three reagent delivery steps, only three examination steps and only three nucleotide types.

Example 2

One Color, Three Nucleotide Types, Two Deliveries

As shown in the first column of Table 2, two flows can be carried out to deliver a total of three nucleotide types to the primed template. Either the polymerase or the nucleotide can be attached to a fluorescent label. Examinations are carried out after each flow. The fluorescent label can be the same for both flows. The signal expected for a stabilized ternary complex formed in the first flow (and detected in the $1^{st}$ exam) will indicate that a ternary complex has been formed but will be ambiguous regarding whether the complex contains an A or G as the next correct nucleotide. The signal expected for a stabilized ternary complex formed in the second flow (and detected in the $2^{nd}$ exam) will indicate that a ternary complex has been formed but will be ambiguous regarding whether the complex contains an A or C as the next correct nucleotide. As is evident from comparison of signals in Table 2 for the two examinations, the presence of a ternary complex where the next correct nucleotide is A, G or C can be determined by disambiguation whereby A is indicated by signal in both examinations, G is indicated by signal in the $1^{st}$ examination and absence of significant signal in the $2^{nd}$ examination, and C is indicated by absence of significant signal in the $1^{st}$ examination and detection of signal in the $2^{nd}$ examination. The nucleotide that was not delivered (i.e. the T nucleotide in this example) is imputed from the absence of significant signal in both of the examinations. Note that absence of signal for T or any other nucleotide may be due to absence of the nucleotide in the flow. Alternatively, the non-detected nucleotide may be present in the flow and capable of forming ternary complexes, albeit ternary complexes that are not detectable (e.g. due to absence of a label on the ternary complex formed with that nucleotide).

TABLE 2

| Step | A | G | C | T |
|---|---|---|---|---|
| Flow pol + A + G | (+) | (+) | (−) | (−) |
| $1^{st}$ Exam | | | | |
| Flow pol + A + C | (+) | (−) | (+) | (−) |
| $2^{nd}$ Exam | | | | |

An advantage of the configuration in Table 2 is that four nucleotides can be distinguished using only one label, a single detection channel, only two reagent delivery steps, only two examination steps, and only three different nucleotides.

Example 3

Two Colors, Six Nucleotide Types, Two Deliveries

Table 3 shows a configuration in which two flows are carried out to deliver nucleotide types having four different bases. However, the ternary complexes that form with two of the bases have alternative labels in either flow. Specifically, ternary complexes that form with the G nucleotide will be red in the first flow and blue in the second flow. Ternary complexes that form with the T nucleotide will be blue in the first flow and red in the second flow. As such, this configuration is carried out using six different nucleotide types. The nucleotides can be attached to the different fluorescent labels in the mixtures exemplified in the first column of Table 3. Examinations are carried out after each flow. The signal expected for a stabilized ternary complex formed in the first flow (and detected in the $1^{st}$ exam) will indicate that a ternary complex has been formed, but a signal detected in the red channel will be ambiguous regarding whether the complex contains an A or G as the next correct nucleotide and a signal detected in the blue channel will be ambiguous regarding whether the complex contains a C or T as the next correct nucleotide. The signal expected for a stabilized ternary complex formed in the second flow (and detected in the $2^{nd}$ exam) will indicate that a ternary complex has been formed but a signal detected in the red channel will be ambiguous regarding whether the complex contains an A or T as the next correct nucleotide and a signal detected in the blue channel will be ambiguous regarding whether the complex contains a G or C nucleotide. As is evident from comparison of signals in Table 3 for the two examinations, the next correct nucleotide can be identified by disambiguation whereby A is indicated by a red signal in both examinations, G is indicated by a red signal in the $1^{st}$ examination and a blue signal in the $2^{nd}$ examination, C is indicated by a blue signal in the $1^{st}$ examination and a blue signal in the $2^{nd}$ examination, and T is indicated by a blue signal in the $1^{st}$ examination and a red signal in the $2^{nd}$ examination.

TABLE 3

| Step | A | G | C | T |
|---|---|---|---|---|
| Flow pol + $A_{red}$ + $G_{red}$ + $C_{blue}$ + $T_{blue}$ | red | red | blue | blue |
| $1^{st}$ Exam | | | | |
| Flow pol + $A_{red}$ + $G_{blue}$ + $C_{blue}$ + $T_{red}$ | red | blue | blue | red |
| $2^{nd}$ Exam | | | | |

An advantage of the configuration in Table 3 is that four nucleotides can be distinguished using only two labels, only two detection channels, only two reagent delivery steps, and only two examination steps. Although six different nucleotides are used in this configuration, an added benefit is improved error checking for all types of nucleotides in the template due to the fact that two different positive signals are detected for each type of next correct nucleotide at a particular position in the template.

The configuration in Table 3 can be modified to use intensity scaling, instead of wavelength differences, to distinguish stabilized ternary complexes. For example, the red labels can be retained and the blue labels can be replaced with red labels that have a fraction of the intensity of the red labels that are retained. An advantage of this modification is that two channel detection can be replaced with simpler and cheaper single channel detection (so long as signal intensities can be distinguished in the single channel).

Example 4

Two Colors, Four Nucleotide Types, Two Deliveries

Table 4 shows a configuration in which two flows are carried out to deliver a total of four nucleotide types to the primed template. The nucleotides can be attached to the different fluorescent labels in the mixtures exemplified in the first column of Table 4. Examinations are carried out after each flow. The signal expected for a stabilized ternary complex formed in the first flow (and detected in the $1^{st}$ exam) will indicate that a ternary complex has been formed, but a signal detected in the red channel will be ambiguous regarding whether the complex contains an A or G as the next correct nucleotide and a signal detected in the blue channel will be ambiguous regarding whether the complex contains a C or T as the next correct nucleotide. A red signal detected in the $2^{nd}$ examination will indicate that A is the next correct nucleotide in the ternary complex and a blue signal will indicate that C is the next correct nucleotide in the ternary complex. As is evident from comparison of signals in Table 4 for the two examinations, the next correct nucleotide can be identified by disambiguation whereby A is indicated by a red signal in both examinations, G is indicated by a red signal in the $1^{st}$ examination and absence of significant signal in the $2^{nd}$ examination, C is indicated by a blue signal in both examinations, and T is indicated by a blue signal in the $1^{st}$ examination and absence of significant signal in the $2^{nd}$ examination.

TABLE 4

| Step | A | G | C | T |
|---|---|---|---|---|
| Flow pol + $A_{red}$ + $G_{red}$ + $C_{blue}$ + $T_{blue}$ | red | red | blue | blue |
| $1^{st}$ Exam | | | | |
| Flow pol + $A_{red}$ + $C_{blue}$ | red | (−) | blue | (−) |
| $2^{nd}$ Exam | | | | |

An advantage of the configuration in Table 4 is that four nucleotides can be distinguished using only two labels, only two detection channels, only two reagent delivery steps, and only two examination steps. Four nucleotide types are used in this configuration, but error checking is provided for two of the nucleotide types in the template due to the fact that two different positive signals are detected for two next correct nucleotide types at a particular position in the template.

The configuration in Table 4 can be modified to use intensity scaling, instead of wavelength differences, to distinguish stabilized ternary complexes. For example, the red labels can be retained and the blue labels can be replaced with red labels that have a fraction of the intensity of the red labels that are retained. An advantage of this modification is that two channel detection can be replaced with simpler and cheaper single channel detection (so long as signal intensities can be distinguished in the single channel).

Example 5

Two Colors, Three Nucleotide Types, Two Deliveries

Table 5 shows a configuration in which two flows are carried out, to deliver a total of three nucleotide types to the primed template. The nucleotides can be attached to the different fluorescent labels in the mixtures exemplified in the first column of Table 5. Examinations are carried out after each flow. The signal expected for a stabilized ternary complex formed in the first flow (and detected in the $1^{st}$ exam) will indicate that a ternary complex has been formed, but a signal detected in the red channel will be ambiguous regarding whether the complex contains an A or G as the next correct nucleotide. A blue signal in the $1^{st}$ examination will indicate that C is the next correct nucleotide. A red signal detected in the $2^{nd}$ examination will indicate that A is the next correct nucleotide in the ternary complex and a blue signal will indicate that C is the next correct nucleotide in the ternary complex. As is evident from comparison of signals in Table 4 for the two examinations, the next correct nucleotide can be identified by disambiguation whereby A is indicated by a red signal in both examinations, G is indicated by a red signal in the $1^{st}$ examination and absence of significant signal in the $2^{nd}$ examination, and C is indicated by a blue signal in both examinations. The nucleotide that was not delivered (i.e. the T nucleotide in this example) is imputed from the absence of significant signal in both of the examinations. Note that absence of signal for T or any other nucleotide may be due to absence of the nucleotide in the flow. Alternatively, the non-detected nucleotide may be present in the flow and capable of forming ternary complexes, albeit ternary complexes that are not detectable (e.g. due to absence of a label on the ternary complex formed with that nucleotide).

TABLE 5

| Step | A | G | C | T |
|---|---|---|---|---|
| Flow pol + $A_{red}$ + $G_{red}$ + $C_{blue}$ | red | red | blue | (−) |
| $1^{st}$ Exam | | | | |
| Flow pol + $A_{red}$ + $C_{blue}$ | red | (−) | blue | (−) |
| $2^{nd}$ Exam | | | | |

An advantage of the configuration in Table 5 is that four nucleotides can be distinguished using only two labels, only two detection channels, only two reagent delivery steps, only two examination steps and only three nucleotide types.

Error checking is provided for two of the nucleotide types in the template due to the fact that two different positive signals are detected for two next correct nucleotide types at a particular position in the template.

The configuration in Table 5 can be modified to use intensity scaling, instead of wavelength differences, to distinguish stabilized ternary complexes. For example, the red labels can be retained and the blue labels can be replaced with red labels that have a fraction of the intensity of the red labels that are retained. An advantage of this modification is that two channel detection can be replaced with simpler and cheaper single channel detection (so long as signal intensities can be distinguished in the single channel).

Example 6

Three Color Detection Schemes

Tables 6 through 8 show several configurations that exploit three different labels detected in three different channels. The configuration in Table 6 uses only three nucleotide types, only three labels and imputation of one unused nucleotide type, thereby providing advantages of requiring no more than one flow and fewer labels (and detection channels) than the number of nucleotides distinguished. Note that absence of signal for T may be due to absence of the T nucleotide in the flow. Alternatively, the T nucleotide may be present in the flow and capable of forming ternary complexes that are not detectable (e.g. due to absence of a label on the ternary complex formed with the T nucleotide).

TABLE 6

| Step | A | G | C | T |
|---|---|---|---|---|
| Flow pol + $A_{red}$ + $G_{yellow}$ + $C_{blue}$ | red | yellow | blue | (−) |
| Exam | | | | |

The configuration in Table 7 uses four nucleotide types, two flows and only three labels, thereby providing an advantage of requiring fewer labels (and detection channels) than the number of nucleotides distinguished. As a further advantage, error checking is provided for three of the nucleotide types in the template due to the fact that three different positive signals are detected at any position in the template.

TABLE 7

| Step | A | G | C | T |
|---|---|---|---|---|
| Flow pol + $A_{red}$ + $G_{yellow}$ + $C_{blue}$ + $T_{red}$ | red | yellow | blue | red |
| 1$^{st}$ Exam | | | | |
| Flow pol + $A_{red}$ + $G_{yellow}$ + $C_{blue}$ | red | yellow | blue | (−) |
| 2$^{nd}$ Exam | | | | |

Table 8 shows a configuration that uses two flows and only three labels, thereby providing an advantage of requiring fewer labels (and detection channels) than nucleotides distinguished. Although five nucleotide types are used, error checking is provided for all four nucleotide types in the template due to the fact that four different positive signals are detectable at any position in the template.

TABLE 8

| Step | A | G | C | T |
|---|---|---|---|---|
| Flow pol + $A_{red}$ + $G_{yellow}$ + $C_{blue}$ + $T_{red}$ | red | yellow | blue | red |
| 1$^{st}$ Exam | | | | |
| Flow pol + $A_{red}$ + $G_{yellow}$ + $C_{blue}$ + $T_{blue}$ | red | yellow | blue | blue |
| 2$^{nd}$ Exam | | | | |

The configurations in Table 6 through 8 can be modified to use intensity scaling, instead of wavelength differences, to distinguish stabilized ternary complexes. For example, the red labels can be retained and the blue and yellow labels can be replaced with red labels that have one third and 2 thirds, respectively, of the intensity of the retained red labels. An advantage of this modification is that three channel detection can be replaced with simpler and cheaper single channel detection (so long as signal intensities can be distinguished in the single channel).

Example 7

Repetitive Examination of Cognate Nucleotides

The flows and exams shown in Tables 1 through 8 can be repeated prior to performing an extension step. The repetitions can lead to the flows and extensions being carried out at least 2, 3, 4, 5 or more times per cycle. Accordingly, a particular position in a template can be repeatedly sampled for ability to form ternary complex with a particular nucleotide type. This repetition can yield a more accurate nucleotide identification than may result absent the repetition. The repetition can also provide a basis for statistical analysis of results and reporting of statistical variance or statistical confidence in the nucleotide calls made at individual positions in a template nucleic acid.

As shown in Table 9, four flows can be carried out, each delivering a different combination of two different nucleotide types, and the result of this combinatorial approach is to evaluate each of the four nucleotide types twice. Either the polymerase or the nucleotide can be attached to a fluorescent label. Examinations are carried out after each flow. The fluorescent label can be the same for both flows. The signal expected for a stabilized ternary complex formed in the first flow (and detected in the 1$^{st}$ exam) will indicate that a ternary complex has been formed but will be ambiguous regarding whether the complex contains an A or G as the next correct nucleotide. The signal expected for a stabilized ternary complex detected in the 2$^{nd}$ examination will be ambiguous regarding whether the complex contains an A or C as the next correct nucleotide. The signal expected for a stabilized ternary complex detected in the 3$^{rd}$ examination will be ambiguous regarding whether the complex contains a G or T as the next correct nucleotide. The signal expected for a stabilized ternary complex detected in the 4$^{th}$ examination will be ambiguous regarding whether the complex contains a C or T as the next correct nucleotide.

TABLE 9

| Step | A | G | C | T |
|---|---|---|---|---|
| Flow pol + A + G | (+) | (+) | (−) | (−) |
| 1$^{st}$ Exam | | | | |
| Flow pol + A + C | (+) | (−) | (+) | (−) |
| 2$^{nd}$ Exam | | | | |

TABLE 9-continued

| Step | A | G | C | T |
|---|---|---|---|---|
| Flow pol + G + T | (−) | (+) | (−) | (+) |
| 3$^{rd}$ Exam | | | | |
| Flow pol + C + T | (−) | (−) | (+) | (+) |
| 4$^{th}$ Exam | | | | |

As is evident from comparison of signals in Table 9 for the four examinations, the presence of a ternary complex where the next correct nucleotide is A, G, C or T can be determined by disambiguation whereby A is indicated by signal in 1$^{st}$ and 2$^{nd}$ examinations, G is indicated by signal in the 1$^{st}$ and 3$^{rd}$ examinations, C is indicated by signal in 2$^{nd}$ and 4$^{th}$ examinations, and T is indicated by signal in 3$^{rd}$ and 4$^{th}$ examinations.

An advantage of this configuration is that each nucleotide type is observed two times per template position (i.e. two times per sequencing cycle). This in turn improves accuracy compared to a configuration where only a single observation is made for each nucleotide type per cycle. Flowing two nucleotides at a time improves speed and reduces reagent cost compared to a configuration where 8 flows and 8 exams are carried out to achieve discrete detection of the 8 individual ternary complexes per cycle.

As shown in Table 10, four flows can be carried out, each delivering a mixture of three nucleotide types, such that all four nucleotide types are evaluated three times each. Again, the polymerase or the nucleotide can be attached to a fluorescent label and examinations are carried out after each flow. The fluorescent label can be the same for both flows. The signal expected for a stabilized ternary complex formed in the first flow (and detected in the 1$^{st}$ exam) will indicate that a ternary complex has been formed but will be ambiguous regarding whether the complex contains an A, G or C as the next correct nucleotide. The signal detected in the 2$^{nd}$ examination will be ambiguous regarding whether the complex contains a G, C or T as the next correct nucleotide. The signal detected in the 3$^{rd}$ examination will be ambiguous regarding whether the complex contains an A, C or T as the next correct nucleotide. The signal detected in the 4th examination will be ambiguous regarding whether the complex contains an A, G or T as the next correct nucleotide.

TABLE 10

| Step | A | G | C | T |
|---|---|---|---|---|
| Flow pol + A + G + C | (+) | (+) | (+) | (−) |
| 1$^{st}$ Exam | | | | |
| Flow pol + G + C + T | (−) | (+) | (+) | (+) |
| 2$^{nd}$ Exam | | | | |
| Flow pol + A + C + T | (+) | (−) | (+) | (+) |
| 3$^{rd}$ Exam | | | | |
| Flow pol + A + G + T | (+) | (+) | (−) | (+) |
| 4$^{th}$ Exam | | | | |

As is evident from comparison of signals in Table 10 for the four examinations, the presence of a ternary complex where the next correct nucleotide is A, G, C or T can be determined by disambiguation whereby A is indicated by signal in 1$^{st}$, 3$^{rd}$ and 4$^{th}$ examinations, G is indicated by signal in the 1$^{st}$, 2$^{nd}$ and 4$^{th}$ examinations, C is indicated by signal in 1$^{st}$, 2$^{nd}$ and 3$^{rd}$ examinations, and T is indicated by signal in 2$^{nd}$, 3$^{rd}$ and 4$^{th}$ examinations.

An advantage of this configuration is that each nucleotide type is observed three times per template position (i.e. two times per sequencing cycle). This in turn improves accuracy compared to a configuration where only a single or double observation is made for each nucleotide type per cycle. Flowing three nucleotides at a time improves speed and reduces reagent cost compared to a configuration where 12 flows and 12 exams are carried out to achieve discrete detection of the 12 individual ternary complexes per cycle.

In a variation on the examples shown in Tables 9 and 10, the ternary complexes that are detected can be distinguishable in each examination based on the type of nucleotide that is present in the complex. Taking as an example Table 9, the A and T nucleotides can form ternary complexes having a red label, whereas the G and C nucleotide can form ternary complexes having blue labels. Using two labels in this way will allow the two ternary complexes that result from each flow to be distinguished from each other in each examination. Similarly, intensity scaling can be used to distinguish different types of ternary complexes in each examination. As such, disambiguation is not necessary and instead one type of ternary complex can be distinguished from the other in each examination to improve accuracy and ease of data analysis.

Note that absence of signal for the non-detected nucleotides during each examination (e.g. C and T in the 1$^{st}$ examination of Table 9) may be due to absence of those nucleotides in the flow. Alternatively, the non-detected nucleotides may be present in the flow and capable of forming ternary complexes that are not detectable (e.g. due to absence of a label on the ternary complex formed with those nucleotides).

Example 8

Error Detection Codes

This example exploits a unique capability of SBB™ methods for the purpose of detecting errors. This is possible because SBB™ methodology does not require irreversible incorporation when determining the next nucleotide in the sequence. Since the examination is reversible, it can be done multiple times with unique combinations of nucleotides and fluorescent labels on the nucleotides to detect when an error has occurred.

Error detection will be demonstrated for an SBB™ method that uses a series of three examinations and two signal states for each cycle. In this example, two nucleotides are flowed in each examination and three unique combinations of nucleotides are used, where one nucleotide is never introduced. Table 11A shows an example examination order and the signal states expected for ternary complexes formed with each nucleotide type. Here the signal states are (+) for presence of a signal and (−) for absence of a signal. Table 11B shows the codeword (also referred to as a digit stream) expected for each nucleotide.

A base call can be made for each cycle based on recognition of a valid codeword shown in Table 11B. If a sequencing cycle for a template results in an invalid codeword (i.e. one that is not shown in Table 11B), then it is known that an error has been made. However, the code is not sufficiently complex for error correction.

TABLE 11A

| Step | A | G | C | T |
|---|---|---|---|---|
| Flow pol + A + C | (+) | (−) | (+) | (−) |
| 1$^{st}$ Exam | | | | |
| Flow pol + A + G | (+) | (+) | (−) | (−) |
| 2$^{nd}$ Exam | | | | |
| Flow pol + C + G | (−) | (+) | (+) | (−) |
| 3$^{rd}$ Exam | | | | |

TABLE 11B

| Base Call | Codeword |
|---|---|
| A | 110 |
| G | 011 |
| C | 101 |
| T | 000 |

In the example shown for Tables 11A and 11B, the T nucleotide is omitted from all flows (or, if present, is non-detectable) and, as such, functions as a 'dark nucleotide' the presence of which is imputed. The nucleotide that is omitted, in this example or other embodiments herein that utilize a dark base, can be selected based on characteristics of the nucleotides. For example, the nucleotide that is omitted can be themost expensive nucleotide or the nucleotide that demonstrates poorest performance in formation or detection of ternary complexes. Relative to the standard SBB™ implementation four exams, each flowing one nucleotide at a time, this encoding scheme provides the advantages of removing one flow/examination, saving time and reagent costs, and providing error detection via signal decoding.

Another option is to perform four examinations, including two nucleotides per examination, with a binary signal state. An advantage of this configuration is that there is no nucleotide that is dark across the entire cycle. This configuration is described in Example 7, and summarized in Table 9. The codewords for each valid base type that arise from the configuration of Table 9 are shown in Table 12.

TABLE 12

| Base Call | Codeword |
|---|---|
| A | 1100 |
| G | 1010 |
| C | 0101 |
| T | 0011 |

Partial error correction, or recovery from error, is possible under the scheme of Tables 9 and 12 when one and only one of examination is suspected, or known, to be erroneous. An examination can be ruled suspect for many reasons, for example, intensity not definitively high or low, image out of focus, etc. Table 13 shows the codewords that would result for each base call in the event of a single suspect examination from the cycle shown in Table 9. A question mark in each codeword denotes the result of a suspect cycle. It is apparent from Table 13 that all four bases can be uniquely called in the event of a single suspect cycle.

TABLE 13

| Base Call | Code word |
|---|---|
| A | ?10 |
| A | 1?0 |
| A | 11? |
| C | ?01 |
| C | 1?1 |
| C | 10? |
| G | ?11 |
| G | 0?1 |
| G | 01? |
| T | ?00 |
| T | 0?0 |
| T | 00? |

In the exemplary configurations of this Example either the polymerase or the nucleotide can be attached to a fluorescent label. The absence of signal for any nucleotide may be due to absence of the nucleotide in the flow. Alternatively, the non-detected nucleotide may be present in the flow and capable of forming ternary complexes, albeit ternary complexes that are not detectable (e.g. due to absence of a label on the ternary complex formed with that nucleotide).

The exemplary configurations of Tables 11A, 11B, 12 and 13 use a detectable signal state (+) and a dark state (−), which provides an advantage of distinguishing four base types using a single detection channel. A variation is to use two detectable signal states, for example, two luminescence wavelengths. Although a second detection channel would add complexity to a detection apparatus, the positive identification of each nucleotide in each flow can provide advantages for improving confidence in base calling.

Example 9

Error Correction Codes

This example further exploits a unique capability of SBB™ methods for the purpose of not only detecting errors but also correcting errors. Since the examination is reversible, it can be done multiple times with unique combinations of nucleotides and fluorescent labels on the nucleotides to not only detect when an error has occurred but to also correct the error.

Error detection and correction is provided using an SBB™ cycle that includes five examinations with two nucleotides per flow/examination. Table 14A shows an example examination order and the signal states expected for ternary complexes formed with each nucleotide type. Here the signal states are (+) for presence of a signal and (−) for absence of a signal. Table 14B shows the codeword expected for each nucleotide.

TABLE 14A

| Step | A | G | C | T |
|---|---|---|---|---|
| Flow pol + A + G | (+) | (+) | (−) | (−) |
| 1$^{st}$ Exam | | | | |
| Flow pol + A + C | (+) | (−) | (+) | (−) |
| 2$^{nd}$ Exam | | | | |
| Flow pol + G + T | (−) | (+) | (−) | (+) |
| 3$^{rd}$ Exam | | | | |
| Flow pol + C + T | (−) | (−) | (+) | (+) |
| 4$^{th}$ Exam | | | | |

TABLE 14A-continued

| Step | A | G | C | T |
|---|---|---|---|---|
| Flow pol + A + T | (+) | (−) | (−) | (+) |
| 5$^{th}$ Exam | | | | |

TABLE 14B

| Base Call | Codeword |
|---|---|
| A | 11001 |
| G | 10100 |
| C | 01010 |
| T | 00111 |

Each one of the valid codewords is at least three edits away from any other valid codeword. If a one-digit error is made, then the closest valid codeword can be found and that nucleotide is selected as the base call for that cycle.

The exemplary configurations of Tables 14A and 14B use a detectable signal state (+) and a dark state (−), which provides an advantage of distinguishing four base types using a single detection channel. A variation is to use two detectable signal states, for example, two luminescence wavelengths. Although a second detection channel would add complexity to a detection apparatus, the positive identification of each nucleotide in each flow can provide advantages for improving confidence in base calling.

Although the cycle shown in Table 14A provides for error correction, a disadvantage is the increased time and reagent use resulting from performing more examinations than the number of nucleotides to be resolved. Another option for error correction and detection that is more efficient from the perspective of number of exams introduces a second dye. The result is an encoding scheme that uses a ternary signal state (first color, second color, and dark) represented by ternary digits in the code.

TABLE 15A

| Step | A | G | C | T |
|---|---|---|---|---|
| Flow pol + A$_{blue}$ + C$_{red}$ | blue | (−) | red | (−) |
| 1$^{st}$ Exam | | | | |
| Flow pol + C$_{blue}$ + G$_{red}$ | (−) | red | blue | (−) |
| 2$^{nd}$ Exam | | | | |
| Flow pol + G$_{blue}$ + T$_{red}$ | (−) | blue | (−) | red |
| 3$^{rd}$ Exam | | | | |
| Flow pol + A$_{red}$ + T$_{blue}$ | red | (−) | (−) | blue |
| 4$^{th}$ Exam | | | | |

TABLE 15B

| Base Call | Codeword |
|---|---|
| A | 2001 |
| G | 0120 |
| C | 1200 |
| T | 0012 |

The configuration in Table 15A uses two-channel detection (red and blue emission), and each of the four nucleotides is provided in two forms (one with a red dye and a second with a blue dye) for a total of eight labeled nucleotides used per cycle. A modification on the two color approach is to conserve nucleotide colors across exams. This would change the previous application so that A and G are always blue, and C and T are always red. The configuration of the cycle is shown in Table 16A and resulting codewords for each valid base call are shown in Table 16B.

TABLE 16A

| Step | A | G | C | T |
|---|---|---|---|---|
| Flow pol + A$_{blue}$ + C$_{red}$ | blue | (−) | red | (−) |
| 1$^{st}$ Exam | | | | |
| Flow pol + C$_{red}$ + G$_{blue}$ | (−) | blue | red | (−) |
| 2$^{nd}$ Exam | | | | |
| Flow pol + G$_{blue}$ + T$_{red}$ | (−) | blue | (−) | red |
| 3$^{rd}$ Exam | | | | |
| Flow pol + A$_{blue}$ + T$_{red}$ | blue | (−) | (−) | red |
| 4$^{th}$ Exam | | | | |

TABLE 16B

| Base Call | Codeword |
|---|---|
| A | 2002 |
| G | 0220 |
| C | 1100 |
| T | 0011 |

In the exemplary configurations of this Example either the polymerase or the nucleotide can be attached to a fluorescent label. The absence of signal for any nucleotide may be due to absence of the nucleotide in the flow. Alternatively, the non-detected nucleotide may be present in the flow and capable of forming ternary complexes, albeit ternary complexes that are not detectable (e.g. due to absence of a label on the ternary complex formed with that nucleotide). The configuration in Tables 15A and 16A can be modified to use intensity scaling, instead of wavelength differences, to distinguish stabilized ternary complexes. For example, the red labels can be retained and the blue labels can be replaced with red labels that have a fraction of the intensity of the red labels that are retained. An advantage of this modification is that two channel detection can be replaced with simpler and cheaper single channel detection (so long as signal intensities can be distinguished in the single channel).

The exemplary configurations of Tables 15A and 16A use two detectable signal states (red and blue) and a dark state (−), which provides an advantage of distinguishing four base types using only two detection channels. A variation is to use three detectable signal states, for example, three luminescence wavelengths. Although a third detection channel would add complexity to a detection apparatus, the positive identification of each nucleotide in each flow can provide advantages for improving confidence in base calling.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method of determining a nucleic acid sequence, comprising:
   (a) contacting a primed template nucleic acid with a series of mixtures for forming ternary complexes, wherein each of the mixtures comprises a polymerase and nucleotide cognates for at least two different base types suspected of being present at the next template position of the template nucleic acid, wherein the mixtures differ by the presence or absence of at least one type of nucleotide cognate;
   (b) monitoring the next template position for ternary complexes formed by the series of mixtures, wherein a signal state indicates presence or absence of ternary complex formed at the next template position by each individual mixture, thereby determining a series of signal states that encodes a base call for the next template position; and
   (c) decoding the series of signal states to distinguish a correct base call for the next template position from an error in the base call.

2. The method of claim 1, wherein the series of signal states comprises an error correcting code.

3. The method of claim 2, wherein the series of mixtures consists of three mixtures and the series of signal states is represented by three digits, each digit representing a signal state obtained from a mixture.

4. The method of claim 3, wherein each of the signal states is represented by a binary digit, and wherein the error correcting code comprises a repetition code.

5. The method of claim 4, further comprising correcting the invalid base call by a majority vote between the three digits.

6. The method of claim 2, wherein the series of mixtures consists of four mixtures and the series of signal states is represented by four digits, each digit representing a signal state obtained from a mixture.

7. The method of claim 6, wherein each of the signal states is represented by a ternary digit, wherein the error correcting code comprises a Hamming code, and wherein the Hamming distance between valid base calls is three.

8. The method of claim 7, further comprising correcting the invalid base call to a valid base call having a code with the closest Hamming distance to the code for the invalid base call.

9. The method of claim 2, wherein the series of mixtures consists of five mixtures and the series of signal states is represented by five digits, each digit representing a signal state obtained from a mixture.

10. The method of claim 9, wherein each of the signal states is represented by a binary digit, wherein the error correcting code comprises a Hamming code, and wherein each valid base call differs from other valid base calls by three digits.

11. The method of claim 1, further comprising correcting the invalid base call to a valid base call having a code with the closest Hamming distance to the code for the invalid base call.

12. The method of claim 1, wherein the decoding of the series of signal states identifies the base call as being an invalid base call.

13. The method of claim 12, further comprising correcting the invalid base call to make a valid base call for the next template position.

14. The method of claim 13, wherein the correcting of the error comprises correlating a suspect signal state in the series of signal states with an aberration in step (a) or (b), and selecting the base call having the expected series of signal states with a change in the suspect signal state.

15. The method of claim 14, wherein the aberration in step (b) is selected from the group consisting of a signal to noise ratio below a predetermined threshold, signal below a predetermined threshold, signal above a predetermined threshold, noise above a predetermined threshold, and detector malfunction.

16. The method of claim 14, wherein the aberration in step (a) is selected from the group consisting of a fluidic delivery malfunction, temperature control malfunction, and reagent quality below a predetermined threshold.

17. The method of claim 1, wherein the series of signal states comprises a repetition code, Hamming code, linear code or parity code.

18. The method of claim 1, wherein each of the signal states is represented by a binary digit.

19. The method of claim 18, wherein the binary digit comprises (i) symbols for presence and absence of a signal; (ii) symbols for signals emitted at two different wavelengths; (iii) symbols for signals having two different intensities; or (iv) symbols for signals resulting from excitation at two different wavelengths.

20. The method of claim 1, wherein each of the signal states is represented by a ternary digit.

21. The method of claim 20, wherein the ternary digit comprises (i) symbols for signals emitted at three different wavelengths; (ii) symbols for signals having three different intensities; or (iii) symbols for signals resulting from excitation at three different wavelengths.

22. The method of claim 1, wherein each of the mixtures comprises nucleotide cognates for at least two and no more than three of four different base types suspected of being in the primed template nucleic acid.

23. The method of claim 1, wherein each of the mixtures comprises nucleotide cognates for at least two and no more than two of four different base types suspected of being in the primed template nucleic acid.

24. The method of claim 1, wherein the mixtures differ by the number or type of label attached to at least one type of nucleotide cognate.

25. The method of claim 1, further comprising:
   (d) adding a next correct nucleotide to the primer of the primed template nucleic acid after step (b), thereby producing an extended primer.

26. The method of claim 25, further comprising repeating steps (a) through (d) for the primed template nucleic acid that comprises the extended primer.

27. The method of claim 25, wherein the next correct nucleotide that is added to the primer is a reversibly terminated nucleotide.

28. The method of claim 27, further comprising repeating steps (a) through (d) for the primed template nucleic acid that comprises the extended, reversibly terminated primer.

29. The method of claim 28, further comprising (e) removing the reversible terminator moiety from the extended, reversibly terminated primer after steps (a) through (d) are repeated.

* * * * *